(12) United States Patent
Lakey et al.

(10) Patent No.: US 8,088,581 B2
(45) Date of Patent: *Jan. 3, 2012

(54) DIFFERENTIAL ENZYMATIC FRAGMENTATION BY WHOLE GENOME AMPLIFICATION

(75) Inventors: Nathan D. Lakey, Chesterfield, MO (US); Jeffrey A. Jeddeloh, Oakville, MO (US); Yulia Korshunova, Clayton, MO (US)

(73) Assignee: Orion Genomics LLC, St. Louis, MO (US)

( * ) Notice: Subject to any disclaimer, the term of this patent is extended or adjusted under 35 U.S.C. 154(b) by 407 days.

This patent is subject to a terminal disclaimer.

(21) Appl. No.: 12/287,725

(22) Filed: Oct. 10, 2008

(65) Prior Publication Data

US 2011/0076726 A1 Mar. 31, 2011

Related U.S. Application Data

(63) Continuation of application No. 11/071,013, filed on Mar. 2, 2005, now Pat. No. 7,459,274.

(60) Provisional application No. 60/549,736, filed on Mar. 2, 2004, provisional application No. 60/648,835, filed on Jan. 31, 2005.

(51) Int. Cl.
*C12Q 1/68* (2006.01)
*C12P 19/34* (2006.01)
*C07H 21/04* (2006.01)

(52) U.S. Cl. .................... 435/6.12; 435/91.2; 536/24.33

(58) Field of Classification Search ............. 435/6, 91.2; 536/22.1
See application file for complete search history.

(56) References Cited

U.S. PATENT DOCUMENTS

| | | | |
|---|---|---|---|
| 5,405,760 A | 4/1995 | Raleigh et al. | |
| 5,635,400 A | 6/1997 | Brenner | |
| 5,786,146 A | 7/1998 | Herman et al. | |
| 5,789,389 A | 8/1998 | Tarasewicz et al. | |
| 5,854,033 A | 12/1998 | Lizardi | |
| 5,871,917 A | 2/1999 | Duffy | |
| 6,200,756 B1 | 3/2001 | Herman et al. | |
| 6,265,171 B1 | 7/2001 | Herman et al. | |
| 6,331,393 B1 | 12/2001 | Laird et al. | |
| 6,498,013 B1 * | 12/2002 | Velculescu et al. | 435/6 |
| 6,514,698 B1 | 2/2003 | Lopez et al. | |
| 6,605,432 B1 | 8/2003 | Huang | |
| 6,777,187 B2 | 8/2004 | Makarov et al. | |
| 6,960,436 B2 * | 11/2005 | Cottrell | 435/6 |
| 7,186,512 B2 * | 3/2007 | Martienssen et al. | 435/6 |
| 2002/0123053 A1 | 9/2002 | Luo et al. | |
| 2003/0099997 A1 | 5/2003 | Bestor | |
| 2003/0129602 A1 | 7/2003 | Huang | |
| 2003/0143599 A1 | 7/2003 | Makarov et al. | |
| 2003/0148290 A1 | 8/2003 | Cottrell | |
| 2003/0165923 A1 | 9/2003 | Li et al. | |
| 2003/0180779 A1 | 9/2003 | Lofton-Day et al. | |
| 2004/0209298 A1 | 10/2004 | Kamberov et al. | |
| 2004/0209299 A1 | 10/2004 | Pinter et al. | |
| 2005/0153316 A1 | 7/2005 | Jeddeloh et al. | |
| 2005/0158739 A1 | 7/2005 | Jeddeloh et al. | |
| 2005/0196792 A1 | 9/2005 | Fodor et al. | |
| 2005/0202490 A1 | 9/2005 | Makarov et al. | |

FOREIGN PATENT DOCUMENTS

| | | |
|---|---|---|
| WO | WO 00/26401 A1 | 5/2000 |
| WO | WO 01/68807 A2 | 9/2001 |
| WO | WO 01/75172 A1 | 10/2001 |
| WO | WO 03/025215 A1 | 9/2002 |
| WO | WO 03/023065 A1 | 3/2003 |
| WO | WO 03/027259 A2 | 4/2003 |
| WO | WO 03/035860 A1 | 5/2003 |
| WO | WO 03/066895 A2 | 8/2003 |
| WO | WO 03/076666 A1 | 9/2003 |
| WO | WO 03/078966 A2 | 9/2003 |
| WO | WO 2004/031402 A2 | 4/2004 |
| WO | WO 2005/085477 A1 | 9/2005 |

OTHER PUBLICATIONS

U.S. Appl. No. 60/453,060, Kamberov et al.
U.S. Appl. No. 60/544,844, Lipshutz et al.
U.S. Appl. No. 60/549,736, Jeddeloh et al.
U.S. Appl. No. 60/551,941, Kamberov et al.
U.S. Appl. No. 60/633,062, Fodor et al.
U.S. Appl. No. 09/713,426, McCombie et al.
U.S. Appl. No. 10/795,667, Kamberov et al.
U.S. Appl. No. 10/971,339, Jeddeloh et al.
U.S. Appl. No. 10/971,986, Jeddeloh et al.
U.S. Appl. No. 11/058,566, Fodor et al.
U.S. Appl. No. 11/071,864, Makarov et al.
Adorjan, Peter et al.; "Tumour class prediction and discovery by microarray-based DNA methylation analysis"; 2002, *Nucleic Acids Research*, vol. 30, No. 5, pp. 1-9.
Altschuler, David et al.; "An SNP map of the human genome generated by reducing representation shotgun sequencing"; 2000, *Nature*, vol. 407, pp. 513-516.
Barker David L. et al.; "Two Methods of Whole-Genome Amplification Enable Accurate Genotyping Across a 2320-SNP Linkage Panel"; 2004, *Genome Research*, vol. 14, pp. 901-907.
Burman, Robert W. et al.; "Hypomethylation of an Expanded *FMR1* Allele is not Associated with a Global DNA Methylation Defect"; 1999, *Am. J. Hum. Genet.*, vol. 65, pp. 1375-1386.
Caldas, Carlos et al.; "Frequent somatic mutations and homozygous deletions of the p16 (*MTS1*) gene in pancreatic adenocarcinoma"; 1994, *Nature Genetics*, vol. 8, pp. 27-32.

(Continued)

*Primary Examiner* — Prabha Chunduru
(74) *Attorney, Agent, or Firm* — Kilpatrick Townsend & Stockton LLP

(57) ABSTRACT

The present invention provides methods for detecting the presence of methylation at a locus within a population of nucleic acids.

23 Claims, 12 Drawing Sheets

OTHER PUBLICATIONS

Chu, Da-Chang et al.; "The Use of Real-Time Quantitative Polymerase Chain Reaction to Detect Hypermethylation of the CPG Islands in the Promoter Region Flanking the GSTP1 Gene to Diagnose Prostate Carcinoma"; 2002, *The Journal of Urology*, vol. 167, pp. 1854-1858.

Craig, B.A. et al.; "Designing Microarrays"; 2001, *Applied Statistics in Agriculture*, Kansas State University, pp. 159-164.

Eads, Cindy A. et al.; "MethyLight: a high-throughput assay to measure DNA methylation"; 2000, *Nucleic Acids Research*, vol. 28, No. 8, 8 pages.

Fraga, Mario F. et al.; "DNA Methylation: A Profile of Methods and Applications"; 2002, *BioTechniques*, vol. 33, pp. 632-649.

Frigola, Jordi et al.; "Methylome profiling of cancer cells by amplification of inter-methylated sites (AIMS)"; 2002, *Nucleic Acids Research*, vol. 30, No. 7, 7 pages.

Genc, B. et al.; "Identification of disease associated genes and tumour class prediction by genome wide microarray-based DNA methylation scanning"; 2001, *The American Journal of Human Genetics*, vol. 69, No. 4, abstract 1635, 1 page.

Hatada, Izuho et al.; "A microarray-based method for detecting methylated loci"; 2002, *J. Hum Genet*, vol. 47, pp. 448-451.

Herman, James G. et al.; "Methylation-specific PCR: A novel PCR assay for methylation status of CpG islands"; 1996, *Proc. Natl. Acad. Sci.*, vol. 93, pp. 9821-9826.

Huang, Tim Hui-Ming et al.; "Methylation profiling of CpG islands in human breast cancer cells"; 1999, *Human Molecular Genetics*, vol. 8, No. 3, pp. 459-470.

Kinzler, Kenneth W. et al.; "Whole genome PCR: application to the identification of sequences bound by gene regulatory proteins"; 1989, *Nucleic Acids Research*, vol. 17, No. 10, pp. 3645-3653.

Lewin, Jorn et al.; "Quantitative DNA methylation analysis based on four-dye trace data from direct sequencing of PCR amplificates"; 2004, *Bioinformatics Advance Access*, vol. 20, No. 0, pp. 1-8.

Li, Long-Cheng et al.; "MethPrimer: designing primers for methylation PCRs"; 2002, *Bioformatics*, vol. 18, No. 11, pp. 1427-1431.

McClelland, Michael et al.; "Effect of site-specific modification on restriction endonucleases and DNA modification methyltransferases"; 1994, *Nucleic Acids Research*, vol. 22, No. 17, pp. 3640-3659.

McrBC Technical Bulletin: NEB Restriction Endonucleases, http://www.neb.com/neb/products/res_enzymes/272.html.

McrBC Technical Bulletin No. M0272, 2001, 2 pages.

Okamoto, Keisei et al.; "Epigenetic changes at the insulin-like growth factor II/H19 locus in developing kidney is an early event in Wilms tumorigenesis"; 1997, *Proc. Natl. Acad. Sci.*, vol. 94, pp. 5367-5371.

Schutte, Mieke et al.; "Abrogation of the Rb/p16 Tumor-suppressive Pathway in Virtually All Pancreatic Carcinomas"; 1997, Cancer Research, vol. 57, pp. 3126-3130.

Singal, Rakesh et al.; "Microsoft Word Macro for Analysis of Cytosine Methylation by the Bisulfite Deamination Reaction"; 2001, Bio Techniques, vol. 30, No. 1, pp. 116-120.

Steigerwald, Sabine D. et al.; "Ligation-mediated PCR improves the sensitivity of methylation analysis by restriction enzymes and detection of specific DNA strand breaks"; 1990, *Nucleic Acids Research*, vol. 18, No. 6, pp. 1435-1439.

Tompa, Rachel et al.; "Genome-Wide Profiling of DNA methylation Reveals Transposon Targets of Chromomethylase3"; 2002, *Current Biology*, vol. 12, pp. 65-68.

Toyota, Minoru et al.; "Identification of Differentially Methylated Sequences in Colorectal Cancer by Methylated CpG Island Amplification"; 1999, *Cancer Research*, vol. 59, pp. 2307-2312.

Wang, C.H. et al.; "Autism DNA methylation profiling using CpG microarrays"; 2001, *The American Journal of Human Genetics*, vol. 69, No. 4, abstract No. 2228, 1 page.

Wei, Susan H. et al.; "Methylation Microarray Analysis of Late-Stage Ovarian Carcinomas Distinguishes Progression-free Survival in Patients and Identifies Candidate Epigenetic Markers"; 2002, *Clinical Cancer Research*, vol. 8, pp. 2246-2252.

Yan, Pearlly S. et al.; "CpG Island Arrays: An Application toward Deciphering Epigenetic Signatures of Breast Cancer"; 2000, *Clinical Cancer Research*, vol. 6, pp. 1432-1438.

Humane Genome Center: Laboratory of Genome Database, pp. 128-132.

Humane Genome Center: Laboratory of Genome Structure Analysis, pp. 133-135.

Humane Genome Center: Laboratory DNA Information Analysis, pp. 136-149.

Humane Genome Center: Laboratory of Sequence Analysis, pp. 150-152.

Humane Genome Center: Laboratory of Functional Genomics, pp. 153-156.

HGM2002; Seventh International Human Genome Meeting, Apr. 2002, 1 page.

Yamada, Yoichi et al.; "A comprehensive analysis of CpG islands reveals methylation imprints on human chromosome 21"; HGM2002 Workshop Abstract No. 13, 1 page.

Yamada, Yoichi et al.; "A comprehensive analysis of CpG islands reveals methylation imprints on human chromosome 21"; HGM2002 Poster No. 89, 1 page.

Yamada, Yoichi et al.; "A comprehensive analysis of Allelic Methylation Status of CpG Islands on Human Chromosome 21q"; 2004, Genome Research, pp. 247-266.

Liang, Gangning et al.; "Identification of DNA methylation differences during tumorigenesis by methylation-sensitive arbitrarily primed polymerase chain reaction"; 2002, *Methods*, vol. 27, pp. 150-155.

Singer-Sam, Judith et al.; "A quantitative HpaII-PCR assay to measure methylation of DNA from a small number of cells"; 1990, Nucleic Acids Research, vol. 18, No. 3, 1 page.

van Steensel, Bas et al.; "Chromatin profiling using targeted DNA adenine methyltransferase"; 2001, *Nature Genetics*, vol. 27, pp. 304-308.

Xiong, L.Z. et al.; "patterns of cytosine methylation in an elite rice hybrid and its parental lines, detected by a methylation-sensitive amplification polymorphism technique"; 1999, *Mol. Gen. Genet*, vol. 261, pp. 439-446.

Chen, Chuan-Mu et al.; "Methylation Target Array for Rapid Analysis of CpG Island Hypermethylation in Multiple Tissue Genomes", 2003, *Am J Pathol.*, vol. 163, No. 1, pp. 37-45.

Tanabe, C. et al.; "Evaluation of a Whole-Genome Amplification Method Based on Adaptor-Ligation PCR of Randomly Sheared Genomic DNA", 2003, *Genes, Chromosomes & Cancer*, vol. 38, pp. 168-176.

\* cited by examiner

| Treatment # | Treatments | | Action on DNA Fragment Class | | |
|---|---|---|---|---|---|
| | Enzyme treatment | Whole Genome Amp. (Yes or NO) | Meth. DNA | Unmeth. DNA | Mutated DNA |
| 1 | MSRE | YES | Uncut | Cut | Uncut |
| 2 | MIRE | YES | Cut | Cut | Uncut |
| 3 | MDRE | YES | Cut | Uncut | - |
| 4 | MSRE & MDRE | YES | Cut | Cut | - |
| 5 | MOCK | YES | Uncut | Uncut | Uncut |
| 6 | MOCK | NO | Uncut | Uncut | Uncut |

MSRE     Methylation Sensitive Restriction Enzyme
MIRE     Methylation Insensitive Restriction Enzyme
MDRE     Methylation Dependent Restriction Enzyme
MSRE & MDRE     Double Digest: MSRE and MDRE
MOCK     No Digestion
MOCK     No Digestion

FIG. 3

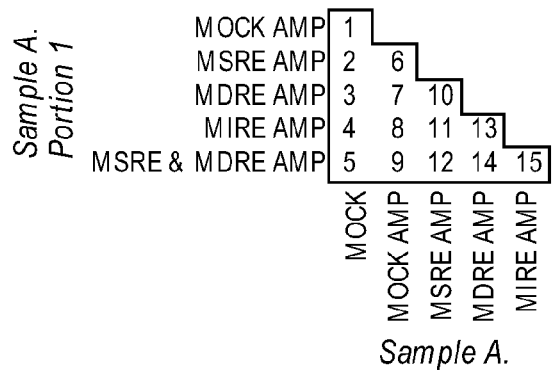

Useful Intra-Sample Comparisons

| Comp-arison | Results |
|---|---|
| 1 | Sequence specific amplification bias |
| 2 | With an understanding of amplification bias, Identify methylated and unmethylated loci |
| 3 | With an understanding of amplification bias, Identify methylated and unmethylated loci |
| 4 | With an understanding of amplification bias, identify mutated loci |
| 5 | Digestion control |
| 6 | Identify methylated and unmethylated loci |
| 7 | Identify methylated and unmethylated loci |
| 8 | Identify mutated loci |
| 9 | Digestion control |
| 10 | Identify methylated and unmethylated loci |
| 11 | Identify mutated, methylated and umethylated loci |
| 12 | Identify methylated and umethylated loci |
| 13 | - |
| 14 | Identify methylated and unmethylated loci |
| 15 | - |

FIG. 4

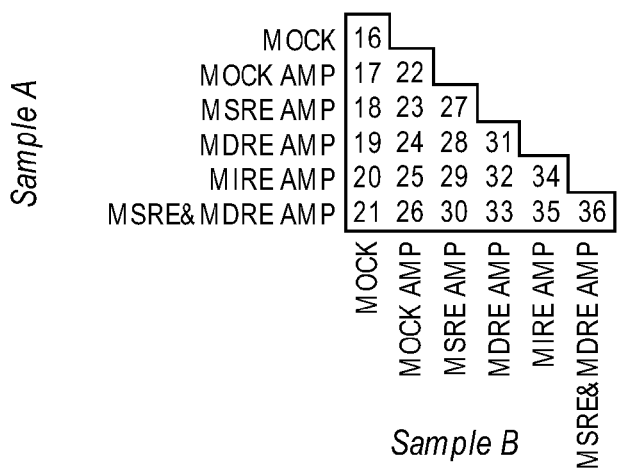

Useful Intra-Sample Comparisons

| Comp-arison | Results |
|---|---|
| 16 | Identify locus copy number differences between the samples |
| 17 | Identify sequence specific amplification bias |
| 18 | With an understanding of amplification bias, Identify methylated and unmethylated loci |
| 19 | With an understanding of amplification bias, Identify methylated and unmethylated loci |
| 20 | With an understanding of amplification bias, Identify mutated loci |
| 21 | Digestion control |
| 22 | Identify locus copy number differences between the samples |
| 23 | Identify methylated and unmethylated loci |
| 24 | Identify methylated and unmethylated loc |
| 25 | Identify mutated loci |
| 26 | Digestion control |
| 27 | Identify differentially methylated, methylated and unmethylated loci |
| 28 | Identify differentially methylated, methylated and unmethylated loci |
| 29 | Identify mutated, methylated and unmethylated loci |
| 30 | Identify differentially methylated, methylated and unmethylated loci |
| 31 | Identify differentially methylated, methylated and unmethylated loci |
| 32 | - |
| 33 | Identify differentially methylated, methylated and unmethylated loci |
| 34 | Identify mutated loci |
| 35 | - |
| 36 | Digestion control |

FIG. 5

FIG. 9
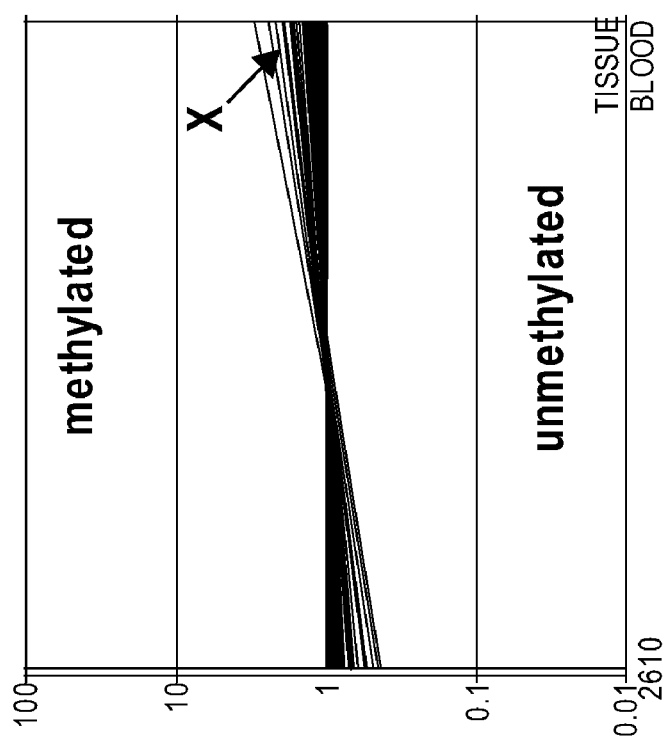
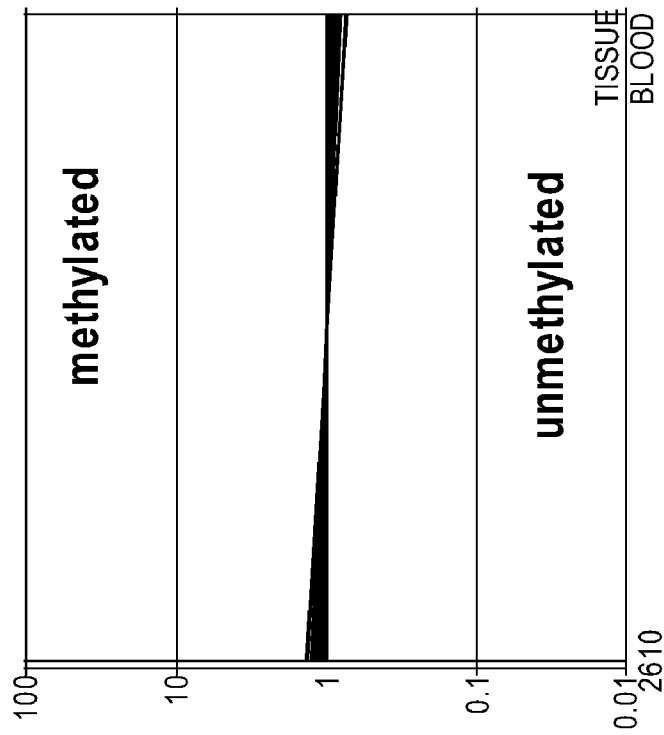
Agilent human 1A(v2) cDNA in situ array
(3' ends of genes on cDNA array)

| | |
|---|---|
| 1kb+ | 1 kilobase DNA ladder (size standard) |
| 1 | No poly-A tail (TdT-), No McrBC digest |
| 2 | No poly-A tail (TdT-), McrBC digested |
| 3 | With poly-A tail (TdT-), No McrBC digest |
| 4 | With poly-A tail (TdT-), McrBC digested |
| 5 | No poly-A tail (TdT-), No McrBC digest |
| 6 | No poly-A tail (TdT-), McrBC digested |
| 7 | With poly-A tail (TdT-), No McrBC digest |
| 8 | With poly-A tail (TdT-), McrBC digested |

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Oligo A for
      creating double stranded sequence tag adapters

<400> SEQUENCE: 1
catggcctat agtgagtcgt attacaattc                                    30

<210> SEQ ID NO 2
<211> LENGTH: 33
<212> TYPE: DNA
<213> ORGANISM: Artificial Sequence
<220> FEATURE:
```

```
<223> OTHER INFORMATION: Description of Artificial Sequence:Oligo B for
      creating double stranded sequence tag adapters

<400> SEQUENCE: 2
tttgaattgt aatacgactc actataggcc atg                                   33

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:tailed DNA
      ligated oligonucleotide poly A tail sequence tag
<220> FEATURE:
<221> NAME/KEY: modified_base
<222> LOCATION: (38)
<223> OTHER INFORMATION: n = g, a, t or c

<400> SEQUENCE: 3
agtggtaaca acgcagagta ctttttttt tttttvn                                38

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Oligo C for
      sequence tag adapters

<400> SEQUENCE: 4
gcctatagtg agtcgtatta caattcgatc                                       30
```

DIFFERENTIAL ENZYMATIC FRAGMENTATION BY WHOLE GENOME AMPLIFICATION

CROSS-REFERENCE TO RELATED APPLICATIONS

The present application is a continuation application of U.S. patent application Ser. No. 11/071,013, filed Mar. 2, 2005, now U.S. Pat. No. 7,459,274, issued Dec. 2, 2008, which claims benefit of priority to U.S. Provisional Patent Application No. 60/549,736, filed Mar. 2, 2004, and U.S. Provisional Patent Application No. 60/648,835, filed Jan. 31, 2005, each of which are hereby incorporated by reference in their entirety for all purposes.

BACKGROUND OF THE INVENTION

DNA typically comprises both methylated and unmethylated bases. Prokaryotic DNA is methylated at cytosine and adenosine residues (see, e.g., McClelland et al., *Nuc. Acids. Res.* 22:3640-3659 (1994). Methylation of prokaryotic DNA protects the DNA from digestion by cognate restriction enzymes, i.e., foreign DNAs (which are not methylated in this manner) that are introduced into the cell are degraded by restriction enzymes which cannot degrade the methylated prokaryotic DNA. DNA methylation patterns can be used to identify specific bacterial types (e.g., genus, species, strains, and isolates).

Mammalian DNA can only be methylated at cytosine residues, typically these cytosines are 5' neighbors of guanine (CpG). This methylation has been shown by several lines of evidence to play a role in gene activity, cell differentiation, tumorigenesis, X-chromosome inactivation, genomic imprinting and other major biological processes (Razin and Riggs eds. in DNA Methylation Biochemistry and Biological Significance, Springer-Verlag, N.Y., 1984).

In eukaryotic cells, methylation of cytosine residues that are immediately 5' to a guanosine, occurs predominantly in CG poor loci (Bird, *Nature* 321:209 (1986)). In contrast, discrete regions of CG dinucleotides called CpG islands remain unmethylated in normal cells, except during X-chromosome inactivation and parental specific imprinting (Li, et al., *Nature* 366:362 (1993)) where methylation of 5' regulatory regions can lead to transcriptional repression.

Aberrant methylation, including aberrant methylation at specific loci, is often associated with a disease state. For example, de novo methylation of the Rb gene has been demonstrated in a small fraction of retinoblastomas (Sakai, et al., *Am. J. Hum. Genet.,* 48:880 (1991)), and a more detailed analysis of the VHL gene showed aberrant methylation in a subset of sporadic renal cell carcinomas (Herman, et al., *PNAS USA,* 91:9700 (1994)). Expression of a tumor suppressor gene can also be abolished by de novo DNA methylation of a normally unmethylated 5' CpG island. See, e.g., Issa, et al., *Nature Genet.* 7:536 (1994); Merlo, et al., *Nature Med.* 1:686 (1995); Herman, et al., *Cancer Res.,* 56:722 (1996); Graff, et al., *Cancer Res.,* 55:5195 (1995); Herman, et al., *Cancer Res.* 55:4525 (1995). Methylation of the p16 locus is associated with pancreatic cancer. See, e.g., Schutte et al., *Cancer Res.* 57:3126-3131 (1997). Methylation changes at the insulin-like growth factor II/H19 locus in kidney are associated with Wilms tumorigenesis. See, e.g., Okamoto et al., *PNAS USA* 94:5367-5371 (1997). The association of alteration of methylation in the p15, E-cadherin and von Hippel-Lindau loci are also associated with cancers. See, e.g., Herman et al., *PNAS USA* 93:9821-9826 (1997). The methylation state of GSTP 1 is associated with prostate cancer. See, e.g., U.S. Pat. No. 5,552,277. Tumors where certain genomic loci are methylated have been found to respond differently to therapies such as cis-platin or radiation treatment than tumors where the same genomic loci are unmethylated. It is clear that DNA from tumor cells at certain genomic loci can be different in the levels of DNA methylation and in this way can be distinguished from the DNA from adjacent normal cells. DNA from tumor cells has been found in various body fluids and other clinical specimens collected from cancer patients. For example, methylated DNA having the same sequence of tumor suppressor genes has been found in serum, urine, saliva, sputum, semen, lavages, cell scrapes, biopsies, resected tissues, and feces. Therefore, detection of altered methylation profiles at loci where such alterations are associated with disease can be used to provide diagnoses or prognoses of disease.

Current methods for determining whether DNA is methylated or unmethylated typically use methylation-sensitive restriction enzymes or a combination of methylation-sensitive and methylation-insensitive restriction enzymes (see, e.g., Burman et al., *Am. J. Hum. Genet.* 65:1375-1386 (1999); Toyota et al., *Cancer Res.* 59:2307-2312 (1999); Frigola et al., *Nucleic Acids Res.* 30(7):e28 (2002); Steigerwald et al., *Nucleic Acids Res.* 18(6):1435-1439 (1990); WO 03/038120; and U.S. Patent Publication No. 2003/0129602 A1). Methylation-sensitive restriction enzymes cleave their cognate DNA recognition sites only if specific nucleotides within those sites are not methylated. Therefore, methods used to detect the presence of DNA methylation following methylation-sensitive restriction enzyme digestion rely on reporting a negative enzymatic outcome. That is, methylation is detected based on the failure of the methylation-sensitive restriction enzyme to cleave its DNA recognition sequence. This strategy introduces the unavoidable caveats of basing a positive experimental measurement on a negative enzymatic outcome (i.e. the result that reports the presence of DNA methylation is equivalent to the result that would occur if the enzyme was absent or inactive due to suboptimal conditions).

In some cases, methylation-sensitive restriction enzymes are used in combination with methylation-insensitive restriction enzymes. Methylation-insensitive restriction enzymes cleave their DNA recognition sites regardless of the presence of DNA methylation. Combining digestion by a methylation-sensitive restriction enzyme with digestion with a methylation-insensitive restriction enzyme that cleaves the same DNA recognition site (an isoschizomer) allows confirmation that the DNA site of interest is susceptible to restriction enzyme digestion in general, but does not alleviate the caveats associated with use of methylation-sensitive enzymes as the sole indicator of the presence of DNA methylation. In addition, these methods act on non-randomly fragmented DNA and can not measure DNA methylation of sequences in much of the genome.

Thus, there is a need in the art for more efficient and more comprehensive methods of detecting methylation of DNA, particularly DNA at specific loci. The present invention addresses these and other needs.

BRIEF SUMMARY OF THE INVENTION

According to the methods of the invention, the methylation state in a DNA sample of at least one locus and potentially hundreds of thousands of loci in parallel can be determined. Sample DNA (e.g., from a cell or tissue sample) is isolated and digested with a methylation-sensitive restriction enzyme, a methylation-dependent restriction enzyme, or a methylation-insensitive restriction enzyme. In general, the use of one of the above enzymes changes the average fragment length of DNA from regions of the genome that differ in DNA methylation density (or in abundance of perfect restriction sites in the case of a methylation-insensitive restriction enzyme), whereby fragments from digested regions will be smaller on average than fragments from undigested regions. This difference in fragment length introduces a bias in a subsequent whole genome amplification step, which is achieved by using one of several techniques. Specific sequences are then quantified in differentially amplified populations resulting from the whole genome amplification step, yielding information about the methylation states of these sequences.

The methods of the invention also provide for the addition of sequence tags to at least one end of the sample DNA fragments, generating modified DNA fragments before the amplification step. In some cases, the sample DNA is already fragmented, and in some cases the sample DNA is fragmented before the adding step. Modified DNA fragments are then digested with a methylation-sensitive restriction enzyme, a methylation-dependent restriction enzyme, a methylation-insensitive restriction enzyme, or with combinations thereof. The fragments are then amplified (i.e., with a whole genome amplification technique) with polynucleotides specific to the added sequence tag, such that digested modified DNA fragments amplify less efficiently than undigested modified DNA fragments, and an amplification bias is introduced.

When digested with a methylation-sensitive restriction enzyme, sequences representing modified DNA fragments that are methylated will be over represented in the final amplification population and sequences representing unmethylated DNA fragments will be under represented in the final amplification population. Therefore, an amplification bias in favor of methylated DNA fragments occurs. Conversely, when digested with a methylation-dependent restriction enzyme, sequences representing modified DNA fragments that are methylated will be under represented in the final amplification population and sequences representing unmethylated DNA fragments will be over represented in the final amplification population. In this way, an amplification bias in favor of unmethylated DNA fragments occurs.

When digested with a methylation-insensitive restriction enzyme, sequences representing modified DNA fragments that have sequence changes (or mutations) at certain recognition sites will be over represented in the final amplification population and sequences representing DNA fragments that do not have sequence changes at certain recognition sites will be under represented in the final amplification population. In this way, an amplification bias in favor of mutated DNA fragments occurs.

The methods of the invention also provide for the quantification of the abundance of specific sequences in amplified DNA populations. The methods of the invention also provide for the generation of several types of amplified populations, and for comparisons to be made between these populations.

The methods of the invention provide for the division of one or more DNA samples into two or more portions and the digestion of each portion with a different restriction enzyme prior to the amplification step. The methods of the invention also provide for comparisons between unamplified and/or amplified portions from a first sample to one another, or for comparisons between unamplified and/or amplified portions from a first sample to unamplified and/or amplified portions from a second sample.

By comparing the extent to which certain specific sequences increase or decrease in relative abundance within certain DNA populations, the methylation state of DNA having the certain sequence in the original DNA sample can be determined.

The present invention provides methods for amplifying unmethylated or methylated DNA fragments in a biological sample. In some embodiments, the methods comprise the steps of
(a) providing randomly fragmented DNA from the biological sample;
(b) adding a sequence tag onto at least one end of the DNA fragments, thereby generating modified DNA fragments;
(c) digesting the DNA fragments with a methylation-dependent restriction enzyme or a methylation-sensitive restriction enzyme to obtain intact DNA fragments and digested DNA fragments; and
(d) after the digesting step, amplifying the intact modified DNA fragments with at least one primer that initiates amplification from the sequence tags, thereby generating amplified intact DNA fragments representing the unmethylated or methylated modified intact DNA fragments in the sample.

In some embodiments, the method further comprises randomly fragmenting DNA from the biological sample before the adding step.

In some embodiments, the adding step comprises ligating a sequence tag to at least one end of the DNA fragments.

In some embodiments, the sequence tags comprise synthetic molecules that exhibit base pairing, wherein the synthetic molecules are selected from the group consisting of peptide nucleic acids and intercalating nucleic acids.

In some embodiments, the adding step comprises adding a homopolymeric sequence tag to at least one of the ends of the DNA fragments with terminal transferase.

In some embodiments, the sequence tags are added before the digesting step.

In some embodiments, the sequence tags are added after the digesting step.

In some embodiments, the digesting step comprises digesting the fragmented DNA with a methylation-sensitive restriction enzyme; and the amplifying step comprises amplifying intact modified fragments having the same sequence as the methylated DNA in the sample.

In some embodiments, the digesting step comprises digesting the fragmented DNA with a methylation-dependent restriction enzyme; and the amplifying step comprises amplifying intact modified fragments having the same sequence as the unmethylated DNA in the sample.

In some embodiments, the amplifying step comprises the polymerase chain reaction.

In some embodiments, the amplifying step comprises rolling circle amplification or branched chain amplification.

In some embodiments, the amplification is linear.

In some embodiments, the method comprises quantifying the number of amplified intact DNA fragments comprising a particular sequence.

In some embodiments, the quantifying step comprises hybridizing the amplified intact DNA to a quantifying polynucleotide.

In some embodiments, the quantifying polynucleotide comprises synthetic molecules that exhibit base pairing.

In some embodiments, the synthetic molecules are selected from the group consisting of peptide nucleic acids and intercalating nucleic acids.

In some embodiments, the quantifying step is performed after the amplifying step and the quantifying step comprises detecting copies of a locus with hybrid capture.

In some embodiments, the quantifying polynucleotide is used in a quantitative amplification step.

In some embodiments, the quantifying polynucleotide is attached to a solid support.

In some embodiments, before the amplifying step, the DNA fragments are contacted with an agent that modifies unmethylated cytosines but does not modify methylated cytosines; and the quantifying step comprises hybridizing a polynucleotide to amplified intact DNA where the polynucleotide hybridizes to the converted sequence.

In some embodiments, the digesting step is performed under conditions that allow for at least some copies of methylated modified DNA fragments to remain intact; and the density of methylation at a locus is determined by comparing the number of intact methylated modified DNA fragments that contain the locus after the digesting step and a control value representing the quantity or density of methylated DNA fragments in a control DNA.

In some embodiments, the method further comprises sequencing the amplified intact DNA fragments.

In some embodiments, the method further comprises cloning the amplified DNA to make a library of sequences representing the unmethylated or methylated DNA in the sample.

In some embodiments, the methylation is at the C4 position of a cytosine, the C5 position of a cytosine within the locus, or at the N6 position of an adenosine within the locus.

The present invention provides methods for amplifying unmethylated or methylated DNA fragments in a biological sample. In some embodiments, the methods comprise the steps of amplifying unmethylated or methylated DNA fragments in a biological sample.

The present invention also provides methods for comparing the methylation state of a specific sequence in one portion of randomly fragmented DNA to the methylation state of the same sequence in at least a second portion of DNA. In some embodiments, the method comprises the steps of:

(a) providing a first and a second portion of DNA, wherein the first portion comprises randomly fragmented DNA;
(b) in the first portion:
   (i) adding a sequence tag onto at least one end of the DNA fragments, thereby generating modified DNA fragments;
   (ii) digesting the DNA fragments with a methylation-dependent restriction enzyme, a methylation-sensitive restriction enzyme, a methylation-insensitive restriction enzyme, or a methylation-sensitive restriction enzyme and a methylation dependent restriction enzyme to obtain intact DNA fragments and digested DNA fragments;
   (iii) after the digesting step, amplifying the intact modified DNA fragments with at least one primer that initiates amplification from the sequence tags;
   (iv) quantifying the number of amplified intact modified DNA fragments comprising the specific sequence; and
(c) comparing the number of amplified intact modified DNA fragments having the specific sequence in the first portion to the number of fragments having the specific sequence in the second portion, thereby determining an increase or decrease in methylation of a specific sequence.

In some embodiments, the first portion and the second portion are from one biological sample.

In some embodiments, the first portion is a portion of genomic DNA from a first biological sample and the second portion is a portion of genomic DNA from a second biological sample.

In some embodiments, the second portion comprises randomly fragmented DNA and the method further comprises before the comparing step:
(i) adding a sequence tag onto at least one end of the DNA fragments in the second portion, thereby generating modified DNA fragments in the second portion;
(ii) digesting the second portion with a methylation-sensitive restriction enzyme to obtain intact DNA fragments and digested DNA fragments;
(iii) amplifying the intact modified DNA fragments in the second portion with at least one primer that initiates amplification from at least one sequence tag; and
(iv) quantifying the number of amplified fragments having a specific DNA sequence in the second portion, thereby determining the number of methylated copies of the locus in the portion corresponding to the specific sequence.

In some embodiments, the second portion comprises randomly fragmented DNA and the method further comprises before the comparing step:
(i) adding a sequence tag onto at least one end of the DNA fragments in the second portion, thereby generating modified DNA fragments in the second portion;
(ii) digesting the second portion with a methylation-dependent restriction enzyme to obtain intact DNA fragments and digested DNA fragments;
(iii) amplifying the intact DNA fragments in the second portion with at least one primer that initiates amplification from at least one sequence tag; and
(iv) quantifying the number of amplified fragments having a specific DNA sequence in the second portion, thereby determining the number of unmethylated copies of the locus in the portion corresponding to the specific sequence.

In some embodiments, the second portion comprises randomly fragmented DNA and the method further comprises before the comparing step:
(i) adding a sequence tag onto at least one end of the DNA fragments in the second portion, thereby generating modified DNA fragments in the second portion;
(ii) amplifying intact DNA in the second portion with at least one primer that initiates amplification from at lease one sequence tag, wherein the second portion is not digested with a restriction enzyme; and
(iii) quantifying the number of amplified fragments having a specific sequence in the second portion, thereby determining the total number of copies of the locus in the portion corresponding to the specific sequence.

In some embodiments, the second portion comprises randomly fragmented DNA and the method further comprises before the comparing step:
(i) adding a sequence tag onto at least one end of the DNA fragments in the second portion, thereby generating modified DNA fragments in the second portion;
(ii) digesting the second portion with a methylation-sensitive restriction enzyme and a methylation-dependent restriction enzyme to obtain intact DNA fragments and digested DNA fragments;
(iii) amplifying intact DNA fragments in the second portion with at least one primer that initiates amplification from at least one sequence tag; and
(iv) quantifying the number of amplified fragments having a specific sequence in the digested second portion, thereby determining the total number of copies of the locus in the portion corresponding to the specific sequence that remain intact after the digesting step.

In some embodiments, the second portion comprises randomly fragmented DNA and the method further comprises before the comparing step:
(i) adding a sequence tag onto at least one end of the DNA fragments in the second portion, thereby generating modified DNA fragments in the second portion;
(ii) digesting the second portion with a methylation-insensitive restriction enzyme to obtain intact DNA fragments and digested DNA fragments;

(iii) amplifying intact DNA fragments in the second portion with primers that initiate amplification from at least one sequence tag; and (iv) quantifying the number of amplified fragments having a specific sequence in the digested second portion, thereby determining the number copies of the locus in the portion corresponding to the specific sequence with mutated methylation insensitive restriction sites.

In some embodiments, the method further comprises before the comparing step, quantifying the number of fragments having the specific sequence in the second portion, wherein the second portion is not digested or amplified.

The present invention also provides methods for amplifying unmethylated or methylated DNA fragments in a biological sample. In some embodiments, the method comprises the steps of:

(a) providing fragmented DNA from the biological sample;
(b) following the fragmenting step, adding a sequence tag onto at least one end of the DNA fragments, thereby generating modified DNA;
(c) digesting the modified DNA with a methylation-dependent restriction enzyme to obtain intact DNA fragments and digested DNA fragments; and
(d) after the digesting step, amplifying the intact DNA fragments with primers that initiate amplification from the sequence tags, thereby generating amplified intact DNA fragments representing the unmethylated DNA in the sample.

In some embodiments, the method comprises fragmenting DNA from the biological sample before the adding step.

In some embodiments, the fragmenting step comprises digesting the DNA with a restriction enzyme.

In some embodiments, the fragmenting step comprises completely digesting the DNA with a restriction enzyme.

In some embodiments, the fragmenting step comprises partially digesting the DNA with a restriction enzyme.

In some embodiments, the adding step comprises ligating a sequence tag to at least one end of the DNA fragments.

In some embodiments, the sequence tags comprise synthetic molecules that exhibit base pairing.

In some embodiments, the synthetic molecules are selected from the group consisting of peptide nucleic acids and intercalating nucleic acids.

In some embodiments, the adding step comprises adding a homopolymeric sequence tag to at least one ends of the DNA fragments with terminal transferase.

In some embodiments, the sequence tags are added before the digesting step.

In some embodiments, the sequence tags are added after the digesting step.

In some embodiments, the amplifying step comprises the polymerase chain reaction.

In some embodiments, the amplifying step comprises rolling circle amplification or branched chain amplification.

In some embodiments, the amplifying step comprises linear amplification.

In some embodiments, the method comprises quantifying the number of amplified intact modified DNA fragments comprising a particular sequence.

In some embodiments, the quantifying step comprises hybridizing the amplified intact DNA to a quantifying polynucleotide.

In some embodiments, the quantifying polynucleotide comprises synthetic molecules that exhibit base pairing.

In some embodiments, the synthetic molecules are selected from the group consisting of peptide nucleic acids and intercalating nucleic acids.

In some embodiments, the quantifying step is performed after the amplifying step and the quantifying step comprises detecting copies of a locus with hybrid capture.

In some embodiments, the quantifying polynucleotide is used in a quantitative amplification step.

In some embodiments, the quantifying polynucleotide is attached to a solid support.

In some embodiments, before the amplifying step, the DNA fragments are contacted with an agent that modifies unmethylated cytosines but does not modify methylated cytosines; and the quantifying step comprises hybridizing a polynucleotide to amplified modified DNA where the polynucleotide hybridizes to the converted sequence.

In some embodiments, the digesting step is performed under conditions that allow for at least some copies of potential restriction enzyme cleavage sites for the methylation-dependent restriction enzyme to remain intact; and the density of methylation at a locus is determined by comparing the number of intact methylated loci, which remain after the digesting step; and a control value representing the quantity or density of methylation in a control DNA.

In some embodiments, the method further comprises sequencing the amplified DNA.

In some embodiments, the method further comprises cloning the amplified DNA to make a library of sequences representing the unmethylated DNA in the sample.

In some embodiments, the methylation is at the C4 position of a cytosine, the C5 position of a cytosine within the locus, or at the N6 position of an adenosine within the locus.

The present invention also provides methods for comparing the methylation state of a specific sequence in one portion of DNA to the methylation state of the same sequence in at least a second portion of DNA, the method comprising:

(a) providing a first and a second portion of DNA, wherein the first portion comprises fragmented DNA;
(b) in the first portion:
  (i) adding a sequence tag onto at least one end of the DNA fragments, thereby generating modified DNA;
  (ii) digesting the modified DNA with a methylation-dependent restriction enzyme, a methylation-insensitive restriction enzyme, or a methylation-dependent restriction enzyme and a methylation-sensitive restriction enzyme to obtain intact DNA fragments and digested DNA fragments;
  (iii) after the digesting step, amplifying the intact DNA fragments with primers that initiate amplification from the sequence tags; and
  (iv) quantifying the number of amplified intact modified DNA fragments comprising the specific sequence; and
(c) comparing the number of amplified intact DNA fragments having the specific sequence in the first portion to the number of fragments having the specific sequence in the second portion, thereby determining an increase or decrease in methylation of a specific sequence.

In some embodiments, the first portion and the second portion are from one biological sample.

In some embodiments, the first portion is from a first biological sample and the second portion is from a second biological sample.

In some embodiments, the second portion comprises fragmented DNA, and the method further comprises before the comparing step:

(i) adding a sequence tag onto at least one end of the DNA fragments in the second portion, thereby generating modified DNA fragments in the second portion;
(ii) digesting the second portion with a methylation-sensitive restriction enzyme to obtain intact DNA fragments and digested DNA fragments;

(iii) amplifying the intact modified DNA fragments in the second portion with at least one primer that initiates amplification from at least one sequence tag; and
(iv) quantifying the number of amplified fragments having a specific DNA sequence in the second portion, thereby determining the number of methylated copies of the locus in the portion corresponding to the specific sequence.

In some embodiments, the second portion comprises fragmented DNA, and the method further comprises before the comparing step:
(i) adding a sequence tag onto at least one end of the DNA fragments in the second portion, thereby generating modified DNA fragments in the second portion;
(ii) digesting the second portion with a methylation-dependent restriction enzyme to obtain intact DNA fragments and digested DNA fragments;
(iii) amplifying the intact DNA fragments in the second portion with at least one primer that initiates amplification from at least one sequence tag; and
(iv) quantifying the number of amplified fragments having a specific DNA sequence in the second portion, thereby determining the number of unmethylated copies of the locus in the sample corresponding to the specific sequence.

In some embodiments, the second portion comprises fragmented DNA, and the method further comprises before the comparing step:
(i) adding a sequence tag onto at least one end of the DNA fragments in the second portion, thereby generating modified DNA fragments in the second portion;
(ii) amplifying intact DNA in the second portion with at least one primer that initiates amplification from at lease one sequence tag, wherein the second portion is not digested with a restriction enzyme; and
(iii) quantifying the number of amplified fragments having a specific sequence in the second portion, thereby determining the total number of copies of the locus in the portion corresponding to the specific sequence.

In some embodiments, the second portion comprises fragmented DNA, and the method further comprises before the comparing step:
(i) adding a sequence tag onto at least one end of the DNA fragments in the second portion, thereby generating modified DNA fragments in the second portion;
(ii) digesting the second portion with a methylation-sensitive restriction enzyme and a methylation-dependent restriction enzyme to obtain intact DNA fragments and digested DNA fragments;
(iii) amplifying intact DNA fragments in the second portion with at least one primer that initiates amplification from at least one sequence tag; and
(iv) quantifying the number of amplified fragments having a specific sequence in the digested second portion, thereby determining the total number of copies of the locus in the portion corresponding to the specific sequence that remain intact after the digesting step.

In some embodiments, the second portion comprises fragmented DNA, and the method further comprises before the comparing step:
(i) adding a sequence tag onto at least one end of the DNA fragments in the second portion, thereby generating modified DNA fragments in the second portion;
(ii) digesting the second portion with a methylation-insensitive restriction enzyme to obtain intact DNA fragments and digested DNA fragments;
(iii) amplifying intact DNA fragments in the second portion with primers that initiate amplification from at least one sequence tag; and
(iv) quantifying the number of amplified fragments having a specific sequence in the digested second portion, thereby determining the number copies of the locus in the portion corresponding to the specific sequence with mutated methylation insensitive restriction sites.

In some embodiments, the method further comprising before the comparing step quantifying the number of fragments having the specific sequence in the second portion, wherein the second portion is not digested or amplified.

The present invention also provides methods for comparing the methylation state of a specific sequence in one portion of DNA from a biological sample to the methylation state of the same sequence in at least a second portion of DNA from a second biological sample. In some embodiments, the method comprises:
(a) providing a first portion of fragmented DNA, and a second portion of DNA from a biological sample;
(b) in the first portion:
(i) adding a sequence tag onto at least one end of the DNA fragments, thereby generating modified DNA fragments;
(ii) digesting the DNA fragments with a methylation-sensitive restriction enzyme to obtain intact DNA fragments and digested DNA fragments; and
(iii) after the digesting step, amplifying the intact modified DNA fragments with at least one primer that initiates amplification from the sequence tags, and
(iv) quantifying the number of amplified intact modified DNA fragments comprising the specific sequence;
(c) comparing the number of amplified intact modified DNA fragments having the specific sequence in the first portion to the number of fragments having the specific sequence in the second portion, thereby determining the increase or decrease in methylation of a specific sequence in two different biological samples.

In some embodiments, the method further comprises before the comparing step quantifying the number of fragments having the specific sequence from the second portion, wherein the second portion is not digested or amplified. In some embodiments, the second portion comprises fragmented DNA, and the method further comprises before the comparing step:
(i) adding a sequence tag onto at least one end of the DNA fragments from the second portion, thereby generating modified DNA fragments in the second portion;
(ii) amplifying intact DNA in the second portion with at least one primer that initiates amplification from at lease one sequence tag, wherein the second portion is not digested with a restriction enzyme; and
(iii) quantifying the number of amplified fragments having a specific sequence in the second portion, thereby determining the total number of copies of the locus in the portion corresponding to the specific sequence.

In some embodiments, the second portion comprises fragmented DNA, and the method further comprises before the comparing step:
(i) adding a sequence tag onto at least one end of the DNA fragments from the second portion, thereby generating modified DNA fragments in the second portion;
(ii) digesting the second portion with a methylation-insensitive restriction enzyme to obtain intact DNA fragments and digested DNA fragments;
(iii) amplifying intact DNA fragments in the second portion with primers that initiate amplification from at least one sequence tag; and
(iv) quantifying the number of amplified fragments having a specific sequence in the digested second portion, thereby determining the number copies of the locus in the portion corresponding to the specific sequence with mutated methylation insensitive restriction sites.

The present invention also provides methods for comparing the methylation state of a specific sequence in one portion of DNA from a biological sample to the methylation state of the same sequence in a second portion of DNA from the same biological sample. In some embodiments, the method comprises:
(a) providing a first and a second portion of DNA from the biological sample, wherein the first portion comprises fragmented DNA;
(b) in the first portion:
    (i) adding a sequence tag onto at least one end of the DNA fragments, thereby generating modified DNA;
    (ii) digesting the modified DNA with a methylation-sensitive restriction enzyme to obtain intact DNA fragments and digested DNA fragments; and
    (iii) after the digesting step, amplifying the intact DNA fragments with primers that initiate amplification from the sequence tags;
(c) in the second portion: quantifying the number of fragments having the specific sequence from the second portion, wherein the second portion is not digested or amplified; and
(d) comparing the number of amplified intact DNA fragments having the specific sequence in the first portion to the number of fragments having the specific sequence in the second portion, thereby determining the increase or decrease in methylation of a specific sequence in a biological sample.

The present invention also provides methods for amplifying methylated or unmethylated DNA from a biological sample, the method comprising:
(a) providing DNA from the biological sample;
(b) digesting the DNA with a methylation-dependent restriction enzyme or a methylation-sensitive restriction enzyme to obtain higher molecular weight DNA fragments and lower molecular weight DNA fragments;
(c) amplifying the digested DNA with random primers, thereby preferentially amplifying the higher molecular weight DNA fragments compared to the lower molecular weight DNA fragments.

In some embodiments, the digesting step comprises digesting the DNA with a methylation-dependent restriction enzyme.

In some embodiments, the digesting step comprises digesting the DNA with a methylation-sensitive restriction enzyme.

In some embodiments, the provided DNA is fragmented DNA.

In some embodiments, the method further comprises fragmenting DNA from the biological sample before the digesting step.

In some embodiments, the fragmenting step comprises fragmenting the DNA with a restriction enzyme.

In some embodiments, the fragmenting step comprises randomly fragmenting the DNA.

In some embodiments, the amplifying step comprises priming single stranded portions of the DNA with a population of polynucleotides wherein the 3' ends of the polynucleotides comprise a random sequence motif and the 5' ends of the polynucleotides comprise a constant sequence motif; and extending the primed polynucleotide with a polymerase. In some embodiments, the amplifying step comprises the polymerase chain reaction.

In some embodiments, the amplifying step comprises rolling circle amplification or branched chain amplification.

In some embodiments, the amplification is linear.

In some embodiments, the method comprises quantifying the number of amplified DNA fragments comprising a particular sequence.

In some embodiments, the quantifying step comprises hybridizing the amplified DNA to a quantifying polynucleotide.

In some embodiments, the quantifying polynucleotide comprises synthetic molecules that exhibit base pairing.

In some embodiments, the synthetic molecules are selected from the group consisting of peptide nucleic acids and intercalating nucleic acids.

In some embodiments, the quantifying step is performed after the amplifying step and the quantifying step comprises detecting copies of a locus with hybrid capture. In some embodiments, the quantifying polynucleotide is used in a quantitative amplification step.

In some embodiments, the quantifying polynucleotide is attached to a solid support.

In some embodiments, before the amplifying step, the DNA is contacted with an agent that modifies unmethylated cytosines but does not modify methylated cytosines; and the quantifying step comprises hybridizing a polynucleotide to the amplified DNA wherein the polynucleotide hybridizes to the converted sequence.

In some embodiments, the digesting step is performed under conditions that allow for at least some copies of methylated DNA fragments to remain higher molecular weight; and the density of methylation at a locus is determined by comparing the number of amplified DNA fragments that contain the locus; and a control value representing the quantity or density of methylated DNA in a control DNA.

In some embodiments, the method further comprises sequencing the amplified DNA.

In some embodiments, the method further comprises cloning the amplified DNA to make a library of unmethylated or methylated DNA.

In some embodiments, the methylation is at the C4 position of a cytosine, the C5 position of a cytosine within the locus, or at the N6 position of an adenosine within the locus.

The present invention also provides methods for comparing the methylation state of a specific sequence in one portion of DNA to the methylation state of the same sequence in at least a second portion of DNA. In some embodiments, the method comprises:
(a) providing a first and a second portion of DNA from a biological sample;
(b) in the first portion:
    (i) digesting the DNA with a methylation-dependent restriction enzyme, a methylation-sensitive restriction enzyme, a methylation-insensitive, or a methylation-sensitive restriction enzyme and a methylation-dependent restriction enzyme to obtain higher molecular weight DNA fragments and lower molecular weight DNA fragments;
    (ii) amplifying the digested DNA with random primers, thereby preferentially amplifying the higher molecular weight DNA fragments compared to the lower molecular weight DNA fragments, and
    (iii) quantifying the number of amplified DNA fragments comprising the specific sequence; and
(c) comparing the number of amplified DNA fragments having the specific sequence in the first portion to the number of fragments having the specific sequence in the second portion, thereby determining an increase or decrease in methylation of a specific sequence.

In some embodiments, the first portion and the second portion are portions of genomic DNA from one biological sample.

In some embodiments, the first portion is from a first biological sample and the second portion is from a second biological sample.

In some embodiments, the method further comprises before the comparing step:
(i) digesting the second portion with a methylation-sensitive restriction enzyme to obtain higher molecular weight DNA fragments and lower molecular weight DNA fragments;
(ii) amplifying the digested DNA in the second portion with random primers, thereby preferentially amplifying the higher molecular weight DNA fragments compared to the lower molecular weight DNA fragments, and
(iii) quantifying the number of amplified fragments having a specific DNA sequence in the second portion, thereby determining the number of methylated copies of the locus in the portion corresponding to the specific sequence.

In some embodiments, further comprising before the comparing step:
(i) digesting the second portion with a methylation-dependent restriction enzyme to obtain higher molecular weight DNA fragments and lower molecular weight DNA fragments;
(ii) amplifying the digested DNA in the second portion with random primers, thereby preferentially amplifying the higher molecular weight DNA fragments compared to the lower molecular weight DNA fragments, and
(iii) quantifying the number of amplified fragments having a specific DNA sequence in the second portion, thereby determining the number of unmethylated copies of the locus in the portion corresponding to the specific sequence.

In some embodiments, the method further comprises before the comparing step:
(i) amplifying the DNA in the second portion with random primers, wherein the second portion is not digested with a restriction enzyme; and
(ii) quantifying the number of amplified fragments having a specific sequence in the second portion, thereby determining the total number of copies of the locus in the portion corresponding to the specific sequence.

In some embodiments, the method further comprises before the comparing step:
(i) digesting the second portion with a methylation-sensitive restriction enzyme and a methylation-dependent restriction enzyme to obtain higher molecular weight DNA fragments and lower molecular weight DNA fragments;
(ii) amplifying the digested DNA in the second portion with random primers, thereby preferentially amplifying the higher molecular weight DNA fragments compared to the lower molecular weight DNA fragments, and
(iii) quantifying the number of amplified fragments having a specific sequence in the digested second portion, thereby determining the total number of copies of the locus in the portion corresponding to the specific sequence that remain high molecular weight after the digesting step.

In some embodiments, the method further comprises before the comparing step:
(i) digesting the second portion with a methylation-insensitive restriction enzyme to obtain higher molecular weight DNA fragments and lower molecular weight DNA fragments;
(ii) amplifying the digested DNA in the second portion with random primers, thereby preferentially amplifying the higher molecular weight DNA fragments compared to the lower molecular weight DNA fragments, and
(iii) quantifying the number of amplified fragments having a specific sequence in the digested second portion, thereby determining the number copies of the locus in the portion corresponding to the specific sequence with mutated methylation insensitive restriction sites.

In some embodiments, the method further comprises before the comparing step:
(i) quantifying the number of fragments having the specific sequence in the second portion, wherein the second portion is not digested or amplified.

The present invention also provides methods for a kit for quantifying the methylation in a locus of genomic DNA, the kit comprising a methylation-dependent restriction enzyme or a methylation sensitive restriction enzyme; reagents to amplify DNA; a polymerase capable of utilizing a DNA template.

In some embodiments, the restriction enzyme is a methylation-sensitive restriction enzyme.

In some embodiments, the restriction enzyme is a methylation-dependent restriction enzyme.

In some embodiments, the restriction enzyme is a methylcytosine-dependent restriction enzyme.

In some embodiments, the restriction enzyme is McrBC, McrA, or MrrA.

In some embodiments, at least one target polynucleotide distinguishes that hybridizes to a converted sequence.

In some embodiments, the kit further comprises reagents sufficient to support the activity of the restriction enzyme.

In some embodiments, the kit further comprises a thermostable DNA polymerase.

In some embodiments, the kit further comprises an agent that modifies unmethylated cytosine.

In some embodiments, the kit further comprises agents able to label nucleic acid sequences.

In some embodiments, the kit further comprises a quantifying polynucleotide.

In some embodiments, the polynucleotide is bound to a solid support.

In some embodiments, the kit further comprises a polynucleotide for participation in a RNA:DNA hybrid.

In some embodiments, the kit further comprises the reagents necessary to detect base-pairing by RNA:DNA polynucleotide hybrid molecules.

These and other embodiments of the invention are further illustrated by the detailed description that follows.

BRIEF DESCRIPTION OF THE DRAWINGS

FIG. 3 illustrates the amplification biases that are introduced by differential enzymatic treatments.

FIG. 4 illustrates the comparisons that may be made between genomic DNA taken from one biological sample.

FIG. 5 illustrates the comparisons that may be made between different biological samples (e.g., two different cells, two different samples from the same tissue in the same individual, two cells of the same type from two different individuals, two different samples from the same tissue in two different same individual, etc.).

FIG. 9 illustrates the results from a clustering analysis performed upon the data sets from FIG. 7. Only the loci that change in methylation between blood DNA and the cancer cell line are shown. The left panel depicts genes that gain methylation in the cell line relative to blood, while the right panel depicts the genes that lose methylation in the cell line relative to blood. Gene X is methylated in blood and loses methylation in the cell line. In this way, quantified sequences from amplified portions from one sample can be compared to quantified sequences from amplified portions of a second sample and the relative methylation density of a locus can be determined.

DETAILED DESCRIPTION OF THE INVENTION

I. Introduction

Figure 1:
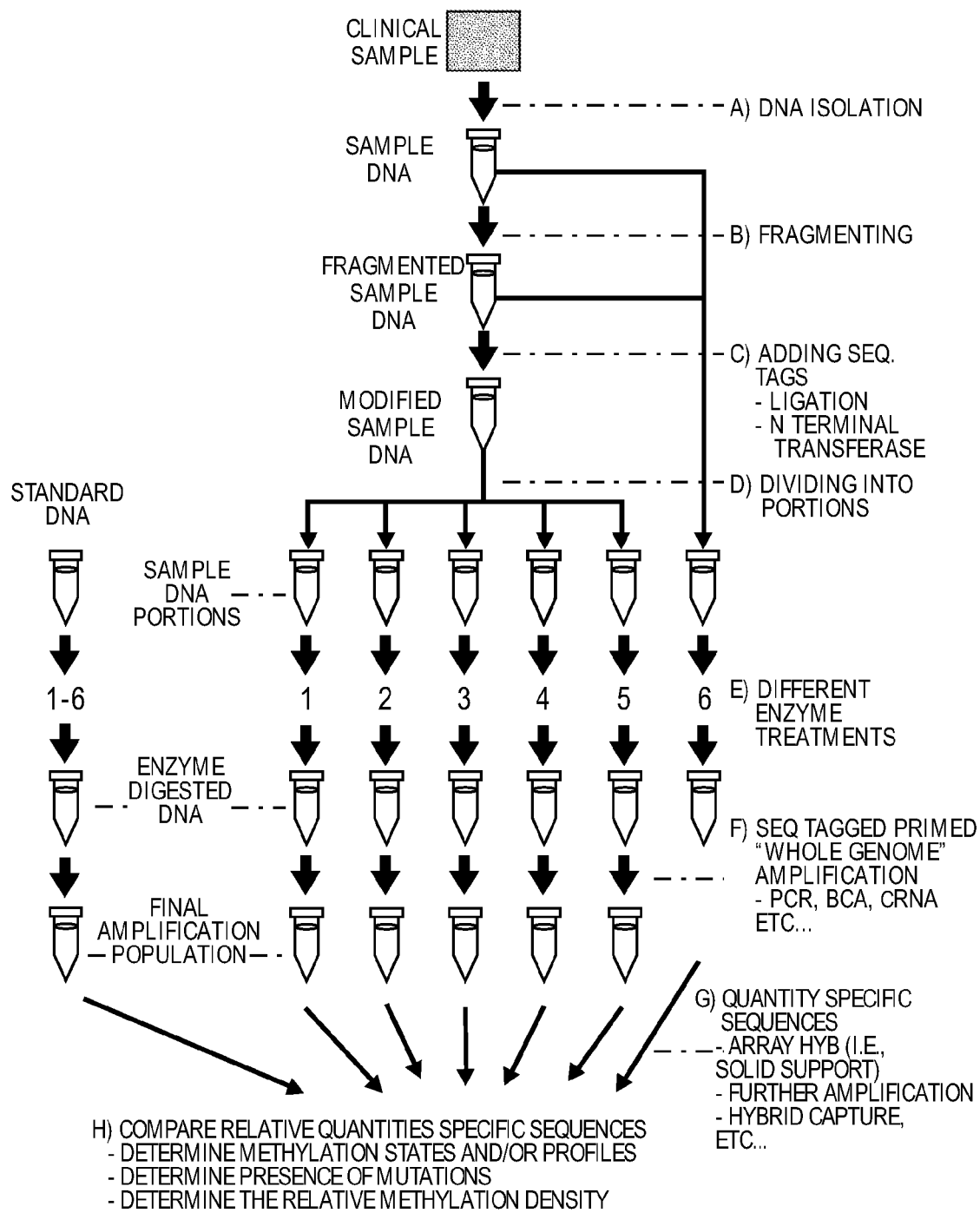
FIG. 1 illustrates one embodiment of the invention of sequence tag mediated amplification of differentially digested DNA from a biological sample.

The present invention provides methods to determine in a DNA sample the methylation state of at least one locus, and of potentially of hundreds of thousands of loci or more in parallel. The invention involves digesting portions of DNA from a sample with various restriction enzymes, thereby introducing a bias detectable in a subsequent amplification step, and then selectively amplifying unmethylated, methylated, or restriction site mutated DNA from the portions, generating amplified populations of DNA. The invention further provides for the quantification of at least one specific DNA sequence. The invention encompasses performing the method to determine more than one (e.g., 10 s, 100 s, 1,000 s) specific DNA sequences in parallel. Finally, the invention provides for comparisons of the final amplified populations to one another.

The methods of the invention can be used, e.g., to identify DNA sequences that are unmethylated or methylated, to determine the methylation profile of one or more cells in a biological sample, to compare methylation profiles of multiple cell populations or multiple samples, to identify genetic polymorphisms (including, e.g., single nucleotide polymorphisms) in a genome, to identify epigenetic polymorphisms in a genome, or to generate libraries of methylated or unmethylated DNA for further analysis (e.g., identifying species homologs or disease-specific methylation of sequences or sequencing to identify the gene coding sequences of a genome). The methods of the invention can be used to discover diagnostic biomarkers in patient samples; or to diagnose disease susceptibility, or the presence of disease; to aid in therapy selection; to monitor disease progression; and to aid in novel target discovery for drug development.

II. Definitions

"Amplifying" DNA refers to any chemical reaction or protein reaction (e.g., enzymatic) that results in an increased number of copies of a template nucleic acid sequence or an increased signal indicating that the template nucleic acid is present in the sample. Amplification can be site specific, or can be accomplished by whole genome amplification (see e.g., U.S. Publication Number 2004/0209299 A1). Amplification reactions include polymerase chain reaction (PCR) and ligase chain reaction (LCR) (see U.S. Pat. Nos. 4,683,195 and 4,683,202; PCR Protocols: A Guide to Methods and Applications (Innis et al., eds, 1990)), strand displacement amplification (SDA) (Walker, et al. *Nucleic Acids Res.* 20(7): 1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313): 91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)). Amplifying includes, e.g., ligating adaptors that comprise T3 or T7 promoter sites to the template nucleic acid sequence and using T3 or T7 polymerases to amplify the template nucleic acid sequence (Sarkar G et al, Nucleic Acids Res. 1992 Sep. 25; 20(18):4937-8, Keohavong P, et al Gene. 1988 Nov. 15; 71(1):211-6, Liu C L et al BMC Genomics. 2003 May 9; 4(1):19), or coupling transcription with branched chain DNA amplification (see e.g., U.S. Pat. No. 6,251,639).

"An agent that modifies unmethylated cytosine" refers to any agent that alters the chemical composition of unmethylated cytosine but does not change the chemical composition of methylated cytosine. Examples of such agents include sodium bisulfite and sodium metabisulfite.

"Biological sample" as used herein refers to a DNA sample obtained from a cell (e.g., a laser capture micro-dissected cell), a population of cells, a clinical specimen from a patient (e.g., blood, blood serum, urine, sputum, feces, sweat, lavages, cell scrapes, biopsies, resected tissue, semen, menstrual fluid, etc.), or from an organism. The organism may be a human, an animal, a plant, a fungus, or a prokaryote.

A "complete digestion" of DNA as used herein refers to contacting DNA with a restriction enzyme for sufficient time and under appropriate conditions to allow for digestion of at least 95%, and typically at least 99%, or all of the restriction enzyme recognition sequences for the particular restriction enzyme. Conditions, including the time, buffers, and other reagents necessary for complete digestions are typically provided by manufacturers of restriction enzymes. Those of skill in the art will recognize that the quality of the DNA sample may prevent complete digestion.

"Concatenated DNA sequences" as used herein refers to serially linked DNA sequences. Typically the concatenated DNA sequences of the present invention comprise fragments (e.g., about 100 to about 50,000 bases) of intact DNA linked to each other. In some embodiments, the fragments are linked to each other via short (e.g., about 5 to about 25 bases) oligonucleotide linkers.

"Dividing" or "divided" in the context of dividing DNA, refers to dividing nucleic acids in a mixture into two or more physically distinct populations. For example, DNA (e.g., genomic DNA) isolated from a sample (e.g., a clinical specimen, cell, tissue, or organ) may be divided into two or more physically distinct "portions," each of which comprise all of the sequences present in the sample.

"Ends" of DNA or of DNA fragments refer to the terminal regions of a DNA molecule. The ends of double stranded DNA may be "blunt" or "sticky." Sticky ends comprise 5' or 3' overhangs of single stranded DNA sequence while blunt ends comprise no overhangs, i.e., they are completely double stranded. In some embodiments, the genomic DNA with sticky ends may be "polished" prior to addition of the sequence tags. "Polished ends" are ends that have had their 3' overhangs degraded and/or the 5' overhangs filled or degraded so that the ends are blunt. "End" may also mean in the case of nicked DNA, the ends of one strand of DNA which is annealed to another strand that is intact in the region of the nick.

An "exonuclease" refers to an enzyme that catalyzes the removal of nucleotides from single- or/and double stranded DNA.

An "exonuclease specific to single-stranded DNA" refers to an exonuclease that catalyzes the removal of nucleotides from single-stranded DNA. One of skill in the art will also appreciate that some exonucleases specific to single-stranded DNA could remove nucleotides from the 5' end as well as the 3'-end of DNA (e.g. Mung Bean nuclease), but some exonucleases specific to single-stranded DNA could remove the nucleotides only from the 3' end (e.g., exonucleaseI) or the 5' end (e.g. exonuclease RedJ$_f$).

An "exonuclease specific to double-stranded DNA" refers to an exonuclease that catalyzes the removal of nucleotides from double-stranded DNA, thereby creating single-stranded DNA. One of skill in the art will also appreciate that some exonucleases specific to double-stranded DNA could remove nucleotides from the 5' end as well as the 3'-end of DNA (e.g. BAL-31), but some exonucleases could remove the nucleotides only from the 3' end (e.g., exonucleaseIII) or the 5' end (e.g. Lambda exonuclease). One of skill in the art will also appreciate that activity of exonucleases specific to double-stranded DNA could be blocked or decreased by modifications of DNA ends (e.g., 3' overhang will block activity of ExoIII nuclease, and dephosphorylation will decrease activity of Lambda exonuclease).

"Fragmentation" refers to any method of introducing single or double stranded breaks in a DNA molecule. Fragmentation can be introduced enzymatically, chemically, mechanically or by any other method available. "Random fragmenting" refers to fragmenting polynucleotides without regard to where fragmentation occurs in a polynucleotide. Thus, random fragmentation does not depend on a specific sequence or methylation state. Accordingly, fragmentation with a restriction enzyme that recognizes a specific sequence before digesting DNA is not random fragmentation.

"Genomic DNA" as used herein refers to DNA extracted from one or more biological samples. Genomic DNA may refer to a population of nucleic acids, which can be mostly intact or mostly fragmented. Multiple genomic DNA populations from different samples may be combined or pooled, resulting in a new, single genomic DNA population. Genomic DNA populations from one may also be divided into portions.

"Isoschizomers" refer to distinct restriction enzymes that have the same recognition sequence. As used in this definition, the "same recognition sequence" is not intended to differentiate between methylated and unmethylated sequences. Thus, an "isoschizomeric partner" of a methylation-dependent or methylation-sensitive restriction enzyme is a restriction enzyme that recognizes the same recognition sequence as the methylation-dependent or methylation-sensitive restriction enzyme regardless of whether a nucleotide in the recognition sequence is methylated. Two isoschizomeric partners are an "isoschizomeric pair."

"Locus" refers to a target sequence within a population of nucleic acids (e.g., a genome). If a single copy of the target sequence is present in the genome, then "locus" will refer to a single locus. If multiple copies of the target sequence are present in the genome, then "locus" will refer to all loci that contain the target sequence in the genome.

"Methylation" refers to cytosine methylation at positions C5 or N4 of cytosine, the N6 position of adenine or other types of nucleic acid methylation. Aberrant methylation of a DNA sequence (i.e., hypermethylation or hypomethylation) may be associated with a disease, condition, or phenotype (e.g., cancer, vascular disease, or cognitive disorders). An "unmethylated" DNA sequence contains substantially no methylated residues at least at recognition sequences for a methylation-dependent restriction enzyme. "Methylated" DNA contains methylated residues at least at the recognition sequences for a methylation-dependent restriction enzyme. It is understood that while a DNA sequence referred to as "unmethylated" may generally have substantially no methylated nucleotides along its entire length, the definition encompasses nucleic acid sequences that have methylated nucleotides at positions other than the recognition sequences for restriction enzymes used in the methods described herein. Likewise, it is understood that while a DNA sequence referred to as "methylated" may generally have methylated nucleotides along its entire length, the definition encompasses nucleic acid sequences that have unmethylated nucleotides at positions other than the recognition sequences for restriction enzymes. In vitro amplified DNA is unmethylated because in vitro DNA amplification methods do not retain the methylation pattern of the amplification template. However, "unmethylated DNA" or methylated DNA" can also refer to amplified DNA whose original template was methylated or unmethylated, respectively.

"Methylation density" refers to the number of methylated residues in a given locus of DNA divided by the total number of nucleotides in the same DNA sequence that are capable of being methylated. Methylation density is determined for cytosines only or adenosines only.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC (see, e.g., U.S. Pat. No. 5,405,760), McrA, MrrA, and Dpnl. One of skill in the art will appreciate that any methylation-dependent restriction enzyme, including homologs and orthologs of the restriction enzymes described herein, is also suitable for use in the present invention.

A "methylation-insensitive restriction enzyme" refers to a restriction enzyme that cleaves at its recognition sequence regardless of the methylation status. Exemplary methylation-insensitive restriction enzymes are described in, e.g., McClelland et al., *Nucleic Acids Res.* 22(17):3640-59 (1994) and http://rebase.neb.com. Suitable methylation-insensitive restriction enzymes that are insensitive to site-specific methylation at position $C^5$ include, e.g., Acu I, All II, Alu I, Ase I, BamH I, Ban II, Bel I, BspM I, Bsr I, BstY I, Dde I, Dra I, EcoN I, Hae III, Hind III, Kpn I, Mse I, Msp I, Nco I, Pst I, Pvu II, Sac I, and Xmn I. One of skill in the art will appreciate that any methylation-insensitive restriction enzyme, including homologs and orthologs of the restriction enzymes described herein, is also suitable for use in the present invention. One of skill in the art will recognize that methylation-insensitive restriction enzymatic actives will be moiety specific and may differ widely in an enzyme specific manner. That is an enzyme that is insensitive to cytosine methylation at or near its recognition sequence may be sensitive to adenine methylation at or near is recognition sequence. For example, Sau3A1 is insensitive to 6 mA within its GATC site but is sensitive to 5 mC at the C position.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., *Nucleic Acids Res.* 22(17):3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I. BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra L Suitable methylation-sensitive restriction enzymes that do not cleave DNA at or near their recognition sequence when an adenosine within the recognition sequence is methylated at position $N^6$ include, e.g., Mho I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3A1 is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

A "methylation profile" refers to a set of data representing the methylation states of one or more loci within a molecule of DNA from e.g., the genome of an individual or cells or tissues from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus.

"Microarray" refers to an ordered or random arrangement of hybridizable array elements. The array elements are arranged so that there are preferably at least one or more different array elements, sometimes at least 100 array elements, and sometimes at least 1,000 array elements per $cm^2$ of substrate surface. Furthermore, the hybridization signal from each of the array elements is typically individually distinguishable. In one embodiment, the array elements comprise polynucleotide sequences.

A "partial digestion" of DNA as used herein refers to contacting DNA with a restriction enzyme under appropriate reaction conditions such that the restriction enzyme cleaves some (e.g., less than about 10%, 20%, 30%, 40%, 50%, 60%, 70%, 80%, or 90%) but not all of possible digestion sites for that particular restriction enzyme in the DNA. A partial digestion of the sequence can be achieved, e.g., by contacting DNA with an active restriction enzyme for a shorter period of time than is necessary to achieve a complete digestion and then terminating the reaction, by contacting DNA with less active restriction enzyme than is necessary to achieve complete digestion with a set time period (e.g., 30, 60, 90, 120, 150, 150, or 240 minutes), or under other altered reaction conditions that allow for the desired amount of partial digestion. "Possible sites" are generally enzyme recognition sequences, but also include situations where an enzyme cleaves at a sequence other than the recognition sequence (e.g., McrBC).

"Primer" refers to a single or double stranded polynucleotide used to hybridize to a template nucleic acid to initiate amplification. Primers may be any length, but are typically between about 4 and about 150 nucleotides in length, more typically between about 8 and about 30 nucleotides in length. Primers are typically single stranded.

"Polynucleotide" refers to a nucleic acid sequence (including but not limited to DNA or RNA), PNA-based sequence (see, e.g., U.S. Pat. No. 6,297,016), intercalating nucleic acid sequence (see, e.g., Christensen, et al., *Nucleic Acids Res.* 30 (22): 4918-4925 (2002)), or sequence of another synthetic molecule exhibiting base pairing, or combinations thereof. Polynucleotides can be single or double-stranded. Polynucleotides can be used (i) as a sequence tag, (ii) as a primer to anneal to (i.e., prime) or to copy or otherwise to amplify a DNA template, or (iii) to quantify a specific sequence within a population of nucleic acid sequences.

"A polynucleotide that hybridizes to a converted sequence" refers to a polynucleotide that:
(i) hybridizes (e.g., are at least partially complementary) to a sequence that represents a methylated DNA sequence after bisulfite conversion, but do not hybridize to a sequence representing the identical unmethylated sequence after bisulfite conversion; or
(ii) hybridizes to a sequence that represents an unmethylated DNA sequence after bisulfite conversion, but do not hybridize to a sequence representing the identical methylated sequence after bisulfite conversion; or
(iii) hybridizes to a sequence that represents an unmethylated DNA sequence after bisulfite conversion, but can not hybridize to a sequence representing the identical methylated sequence because the sequence does not contain sequence motifs capable of being methylated by the cell.

As described herein, polynucleotides that distinguish between methylated and unmethylated sequences are generally designed to hybridize to a sequence that would occur if the DNA was treated with an agent (such as sodium bisulfite) that modifies unmethylated nucleotides but not methylated nucleotides or vice versa. For example, when sodium bisulfite is contacted to DNA, unmethylated cytosine is converted to uracil, while methylated cytosine is not modified. Since uracil forms complements with adenine, a primer that binds to the unmethylated sequence would contain adenines at locations, where the adenines would form complements with the modified cytosines (i.e., uracils). Similarly, if a primer that hybridized to sequences containing methylated cytosines was desired, the primer would contain guanosines, where it would form complements with the methylated cytosines. Thus, sequences that "represent" methylated or unmethylated DNA include DNA that result from sodium bisulfite treatment of the DNA.

"Quantifying the number" of DNA fragments can comprise determining the exact or approximate number of particular fragments in a sample or portion or determining the relative amount of fragments compared to a second known or unknown value. For example, determining the ratio or relative amount of fragments in two samples is considered "determining the number" of fragments in one sample.

A "recognition sequence" refers to a primary nucleic acid sequence and does not reflect the methylation status of the sequence.

"Selective amplification" or "selectively amplifying" refers to amplification of particular sequences in a population of sequences. For example, unmethylated DNA sequences or methylated DNA sequences in a mixed population of DNA sequences (i.e., a population containing both methylated and unmethylated DNA sequences) can be selectively amplified using the methods of the invention. In addition, DNA sequences that have point mutations at recognition sequence sites in a mixed population of DNA sequences (i.e., a population containing both methylated and unmethylated DNA sequences) can be selectively amplified using the methods of the invention.

"Sequence tag" refers to a polynucleotide and may be, e.g., an adaptor hetero-polymeric oligonucleotide or homo-polymeric oligonucleotide sequence that is ligated to the ends of a DNA sequence or may be a homo-polymeric oligonucleotide sequence that is added to the ends of a DNA sequence using a terminal transferase. Sequence tags may be any length, but are typically between about 4 and about 150 nucleotides in length, and more typically between about 8 and about 30 nucleotides in length.

"Solid support" as used herein refers to any material to which a polynucleotide can be attached or any material that can be modified so that a polynucleotide can be attached to it. Solid supports may be planar (e.g., microarrays) or may have three dimensional structure (e.g., beads, gel matrices, membranes). Suitable materials for a solid support include, for example, glass and modified or functionalized glass, inorganic and organic polymers, nylon or nitrocellulose, resins, silica or silica-based materials including silicon and modified silicon, carbon, metals. Illustrative solid surfaces or solid supports include, e.g., nitrocellulose, nylon, glass, quartz, diazotized membranes (paper or nylon), silicones, polyformaldehyde, cellulose, polyacrylamide and cellulose acetate. Where the solid surface or solid support is porous, various pore sizes may be employed depending upon the nature of the system. Suitable materials for planar solid supports (e.g., microarrays) are described in, e.g., U.S. Pat. Nos. 6,558,907 and 6,534,270. Suitable beads are described in, e.g., WO 02/065123; WO 02/064829; WO 01/25002; WO 01/25758; and U.S. Patent Publication No. 20020119470 A1 and include, for example, spheres, beads, dust, and other nanofabricated particles.

"Specifically hybridizes" or "selectively hybridizes" as used herein refers to the binding or hybridizing of a polynucleotide to a particular nucleotide sequence under appropriate hybridization conditions.

The phrase "stringent hybridization conditions" refers to conditions under which a polynucleotide will hybridize to its target nucleic acid sequence (e.g., primer to adaptor or linker; or amplified, unmethylated DNA to a polynucleotide on a solid support), typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion (or other salts), typically about 0.001 to 1.0 M sodium ion, more typically about 800 nM sodium ion at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as follows: ramp temperature 2° C./sec to 80° C., 75° C. for 1 min, 70° C. for 1 min, 65° C. for 1 min, 60° C. for 1 min, 55° C. for 1 min, 50° C. for 1 min, 40° C. for 1 min, 35° C. for 1 min, 30° C. for 1 min, and 25° C. for 1 min. After hybridization, the solution is held at 4° C. prior to wash with NaCl solution.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of about 30 seconds to about 2 minutes at 90° C.-95° C., an annealing phase of about 5 seconds to about 2 minutes at 50° C.-70° C., and an extension phase of about 1 minute to about 5 minutes at about 70° C.

Cleaving, or digesting, DNA "under conditions that allow for at least some copies of potential restriction enzyme cleavage sites in the locus to remain uncleaved" refers to any combination of reaction conditions, restriction enzyme and enzyme concentration, and/or DNA resulting in at least some of the DNA comprising a potential restriction enzyme cleavage site to remain uncut. For example, a partial digestion of the DNA (e.g., by limiting the amount of enzyme or the amount of time of the digestion) allows some potential restriction enzyme cleavage sites in the locus to remain uncut. In some embodiments, the uncut DNA is at least 1, 10, 50, 100, 500, 1000, or more fragments that comprise a restriction enzyme recognition sequence. Alternatively, a complete digestion using a restriction enzyme such as McrBC will result in some potential restriction enzyme cleavage sites in the locus to remain uncleaved because the enzyme does not always cleave between the two recognition half sites, thereby leaving at least some uncleaved copies of a locus in a population of sequences wherein the locus is defined by the two recognition half-sites. A "potential restriction enzyme cleavage site" refers to a sequence that a restriction enzyme is capable of cleaving (i.e., comprising the appropriate nucleotide sequence and methylation status) when it recognizes the enzymes recognition sequence, which may be the same or different from the cleavage site.

III. Methods of the Invention

A. DNA Samples

Most species have genomic DNA methylation. Methylation can occur as 6-methyl adenine (6 mA), 4-methyl cytosine (4 mC), or 5-methyl cytosine (5 mC). DNA methylation is ubiquitous across nearly every kingdom, phylum, order, and class, suggesting that it is evolutionarily important. Some prokaryotic species do not methylate at all, but they are rare. For example, it is believed that 6 mA only appears in prokaryotes and archae. Fungal genomes tend to look more like animal and plant genomes than prokaryotic genomes since they exhibit 5 mC methylation. It has been observed that budding yeast do not exhibit any methylation, but other filamentous fungi do. Further, among animals, some invertebrates do not show any methylation patterns (some nematodes and some insects), but they represent the exception and appear to be particular outliers. For example, while *D. melanogaster* and *A. gamimibie* (insects, fruit flies and mosquitoes) do not appear to have any methylation patterns in their genomes, honeybees do. All vertebrate species (which includes all mammals) and plants exhibit DNA methylation. Even organisms such as viruses show methylation patterns within their genomes. The present invention provides methods for selectively amplifying unmethylated or methylated DNA from any organism with a methylated genome.

Genomic DNA can be isolated from a biological sample (e.g., a cell, a tissue, or an organ) using any means known in the art (e.g., as described in Sambrook et al. 2001, supra and Ausubel et al. 1994, supra). The genomic DNA may be isolated from a single sample (e.g., one cell) or from at least two samples of different types (e.g., two different cells, two different samples from the same tissue in the same individual, two cells of the same type from two different individuals, two different samples from the same tissue in two different same individual, etc.). In some cases, genomic DNA may be isolated from a biological sample from a single organism (e.g., genomic DNA from a blood serum sample). In some cases, the genomic DNA may be isolated from the same biological sample from two different sources (e.g., a section of lung tissue from two different humans). In some cases, the genomic DNA may be isolated from two different biological samples from the same human (e.g., genomic DNA from a biological sample of cancerous lung tissue and a biological sample of adjacent apparently normal lung tissue from the same human).

DNA obtained from any biological sample can be used, e.g., from cells, tissues, and/or fluids from an organism (e.g., an animal, plant, fungus, prokaryote). The samples may be fresh, frozen, dried, preserved in fixative (e.g., alcohol, formaldehyde, paraffin, or PreServeCyte™) or diluted in a buffer. Biological samples include resected tissues; biopsies (from e.g., lung, colon, breast, prostate, cervix, liver, kidney, brain, stomach, esophagus, uterus, testicle, skin, bone, kidney, heart, gall bladder, and bladder); body fluids or secretions (e.g., blood, urine, mucus, sputum, saliva, marrow, feces, sweat, semen, and condensed breath); surgical washings (e.g., bronchoalveolar lavage, ductal lavage, surgical lavage); and cell scraps (e.g., buccal swabs, cervical smear specimens, etc.). Biological samples also include leaves, stems, roots, seeds, petals, pollen, spore, mushroom caps, and sap.

Sample DNA may be well preserved remaining high in molecular weight, partially fragmented or severely fragmented in the sample acquisition or storage process, or in the DNA isolation process.

B. Fragmenting Methods

Once isolated, the sample DNA may be further fragmented. The sample DNA may be sheared or otherwise randomly fragmented (e.g., mechanically, enzymatically or with a chemical agent such as, for example, iron-EDTA sodium bisulfate or hydrazine). The random shearing or fragmentation can cause single and/or double-stranded breaks in the DNA. Fragmenting only one strand of double stranded DNA may be achieved by random nicking by a chemical agent or an endonuclease such as DNAase I or micrococcal nuclease; nicking by f1 gene product II or homologous enzymes from other filamentous bacteriophage (Meyer and Geider, Meyer, *Nature* 278(5702):365-7 (1979)); and/or chemical nicking of the template directed by triple-helix formation (Grant et al. *Biochemistry* 35(38):12313-9 (1996)). See also, U.S. Patent Publication No. US 2003/0143599 A1.

As an alternative to random fragmentation, the sample DNA may be non-randomly fragmented. Non-random fragmentation can be accomplished through treatment with restriction enzymes to completely digest or partially digest a DNA sample. The restriction enzymes can be methylation-sensing or non-sensing restriction enzymes. Since restriction enzymes cleave at predictable sites (e.g., at or near the fixed positions of restriction enzyme recognition sites in the DNA sample in the genome), restriction digests result in a non-random fragmentation of the DNA sample. Typically, a partial digestion reaction is accomplished by preventing an enzyme from cleaving at every recognition sequence contained in a DNA sample in the appropriate methylation state. Most typically, partial digestions are accomplished by limiting the amount of enzyme added to the digestion reaction or limiting the amount of time the reaction is carried out. Alternatively, salinity, pH, temperature, pressure and other environmental parameters can be altered to prevent a digestion from progressing to completion. As a result of either hill or partial enzyme digestions a fragmented population of genomic DNA with defined sequence ends, such as sticky ends or blunt ends, is obtained.

C. Adding Sequence Tags

Once genomic DNA has been isolated, sequence tags may be added to the ends of the genomic DNA. Typically the sequence tags are single or double stranded polynucleotide sequences of about 5 to about 150, e.g., about 10 to about 40, e.g., about 15 to about 30, e.g., about 20 to about 25 nucleotides in length. The sequence tags may include natural (i.e., A, G, C, or T) or synthetic nucleotide bases. One of skill in the art will appreciate that the sequence tags may comprise any molecule able to base pair with DNA (e.g., intercalating nucleic acids, thioester-containing nucleic acids, or peptide nucleic acids). Double stranded tags may be blunt ended, or may have 3' or 5' overhangs, or any combination thereof.

In some embodiments, the sequence tags are homopolymeric-nucleotide sequences. The homopolymeric-nucleotide sequences are typically added to the ends of the genomic DNA using a terminal transferase, e.g., to synthesize a polyA, a polyC, a polyG, or a polyT sequence onto the end of a DNA fragment. The homopolymeric-nucleotide sequences can also be ligated to the genomic DNA. A homopolymeric-nucleotide may include natural (i.e., A, G, C, or T) or synthetic nucleotide bases.

In other embodiments, the sequence tags are polynucleotide adaptors (i.e., heteropolymeric-nucleotides or homopolymeric-nucleotides). The adaptors are ligated to the genomic DNA prior to the amplification step, and are most typically added to the DNA fragment before digesting the genomic DNA with a methylation-dependent or methylation-sensitive restriction enzyme. Synthesis of polynucleotides is well known to those of skill in the art. For example, oligonucleotides can be chemically synthesized according to the solid phase phosphoramidite triester method first described by Beaucage and Caruthers, *Tetrahedron Lens.* 22:1859-1862 (1981), or using an automated synthesizer, as described in Van Devanter et. al., *Nucleic Acids Res.* 12:6159-6168 (1984).

In some cases, the sequence tags include a restriction enzyme recognition sequence, e.g., for cloning of DNA modified with sequence tags, or promoter elements for converting the sequence tagged DNA into RNA, e.g., T7 or T3 bacterial promoter elements.

In some embodiments, the sequence tags can comprise a random portion (e.g., to allow for hybridization to random single-stranded sequence) and a known portion (e.g., to act as a primer binding site for amplification). The sequence tags may be introduced after a single-stranded nick is made in the DNA molecule followed by treatment with a polymerase with 5'→3' exonuclease activity and addition (e.g., ligation) of the sequence tag. See, e.g., U.S. Pat. No. 6,777,187.

Figure 2:
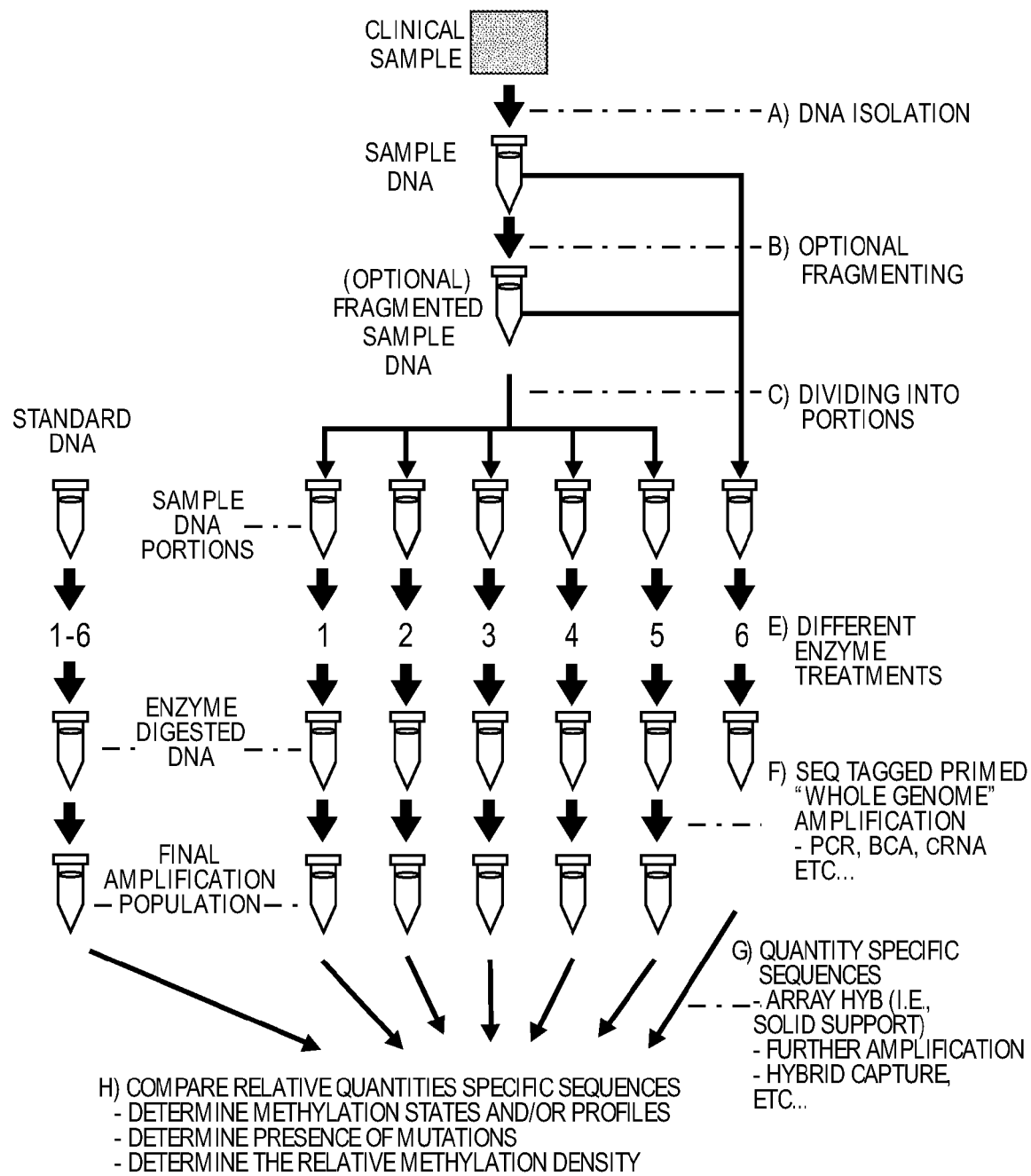
FIG. 2 illustrates one embodiment of the invention of random primed mediated amplification of differentially digested DNA from a biological sample.
Figure 6:
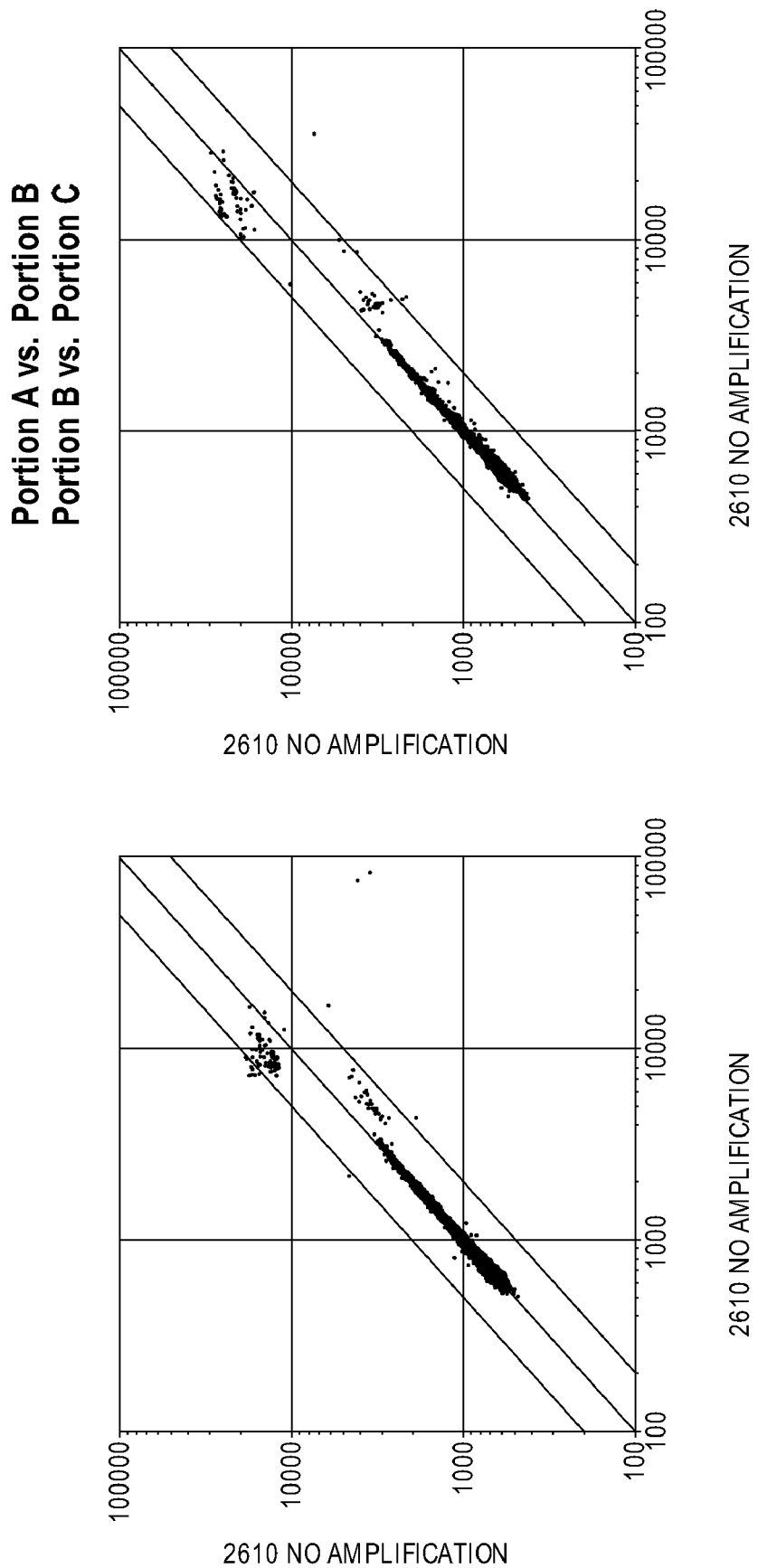
FIG. 6 illustrates the uniformity of the amplification of portions using the method. Whole genomic, sheared DNA (i.e., undigested and unamplified) was aliquoted into four portions. Two portions were independently labeled with a "red" dye and two portions were independently labeled with a "green" dye. The first red portion was mixed with the first green portion and hybridized to an array (e.g., Agilent Catalog 1 human cDNA deposition array). Similarly, the second red portion was mixed with the second green portion and hybridized to a second array. The left panel depicts representative microarray hybridization data obtained utilizing an Agilent Catalog 1 human cDNA deposition array in a dye-swapping experimental design including hybridizations of the two reciprocal red/green labeled combinations described above. The hybridization targets were derived from labeling independent shearing events of the ATCC 2610 genome (self vs. self). The panel on the right depicts a similar analysis, except undigested, but amplified whole genomic, sheared DNA was utilized. The dye swap for portion two consisted of three independent repetitions of the procedure (e.g., array one was hybridized to portion A red vs. portion B green and array two was hybridized to portion B red vs. portion C green). The degree to which the ratio of signal intensities falls along the diagonal 1.0 ratio line is an indication that the method uniformly represents these >14,000 genomic locations. Lines flanking the 1.0 ratio diagonal represent two-fold change thresholds. The small clusters of datapoints at the signal intensity extremes of each plot represent hybridization to control probes represented on the Agilent Catalog 1 human cDNA array.
Figure 7:
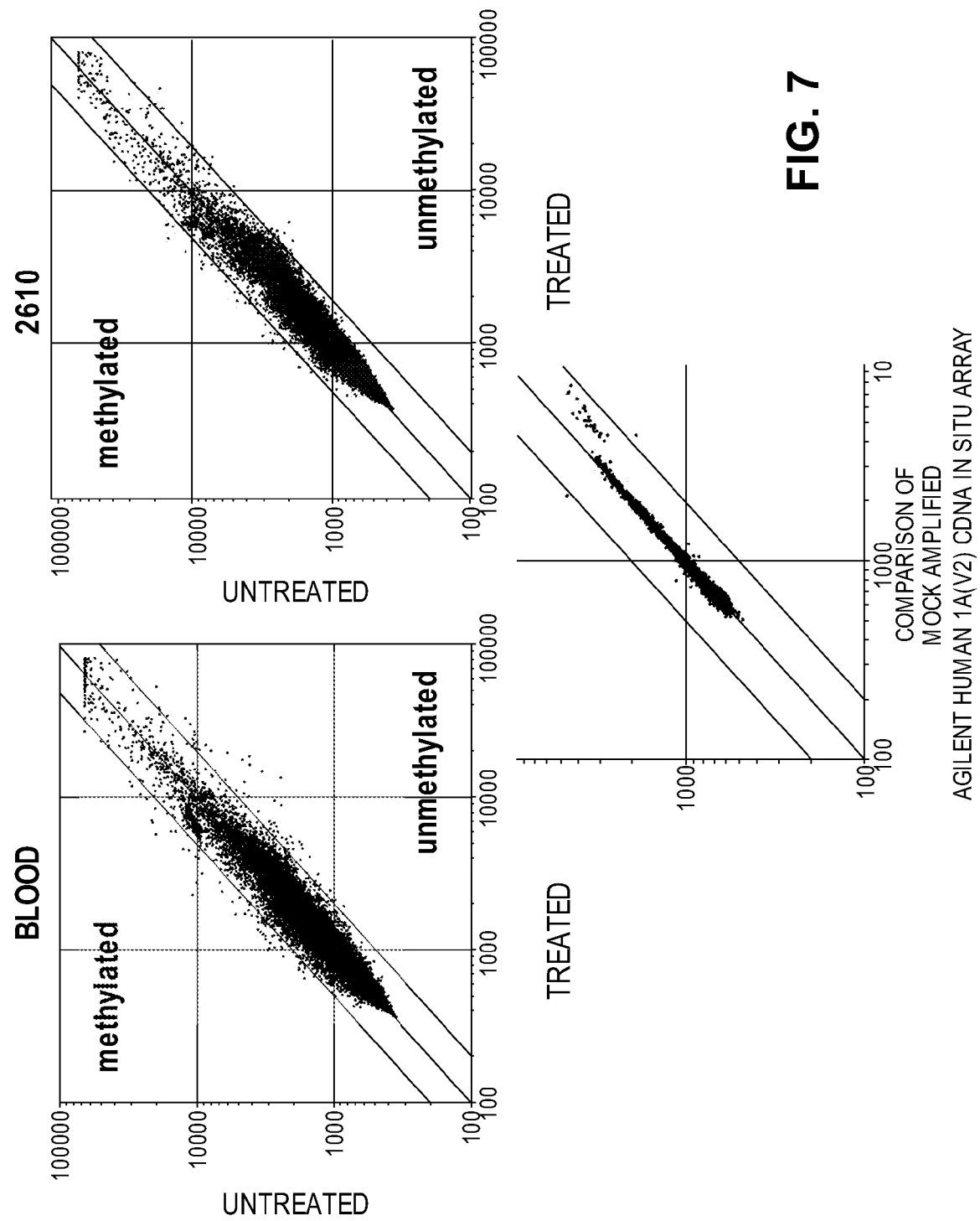
FIG. 7 illustrates the identification of methylated loci within a single sample. Male blood DNA, and glioma cell line DNA (ATCC#2610) was processed according to the method set forth in Example 1. The left panel is the signal intensity plot obtained when a dye swap designed experiment was employed comparing portion 3 (i.e., the methylation-dependent digested and amplified portion) with portion 5 (i.e., the mock treated and amplified portion) derived from blood DNA. The right panel depicts the results of the same procedure when performed upon genomic DNA isolated from the glioma derived cell line ATCC2610. The deviation of the signal intensity ratios away from the 1.0 ratio diagonal line reflects the detection of DNA methylation events in the two samples. Data points that skew to the upper left represent loci in the genome that are methylated and that correspond to specific sequences on the array. Data points that skew to the lower right of the 1.0 ratio diagonal line represent loci in the genome that are unmethylated regions. The distance from the 1.0 line corresponds to the amount of methylation at a specific locus. Therefore, two portions from the same sample (that is, the undigested amplified DNA and the methylation-dependent digested amplified DNA) can be compared to one another, and the presence and density of methylation at a locus can be determined. For comparison, the signal intensity plot obtained by comparison of ATCC2610 DNA without amplification is shown in the lower panel.
Figure 8:
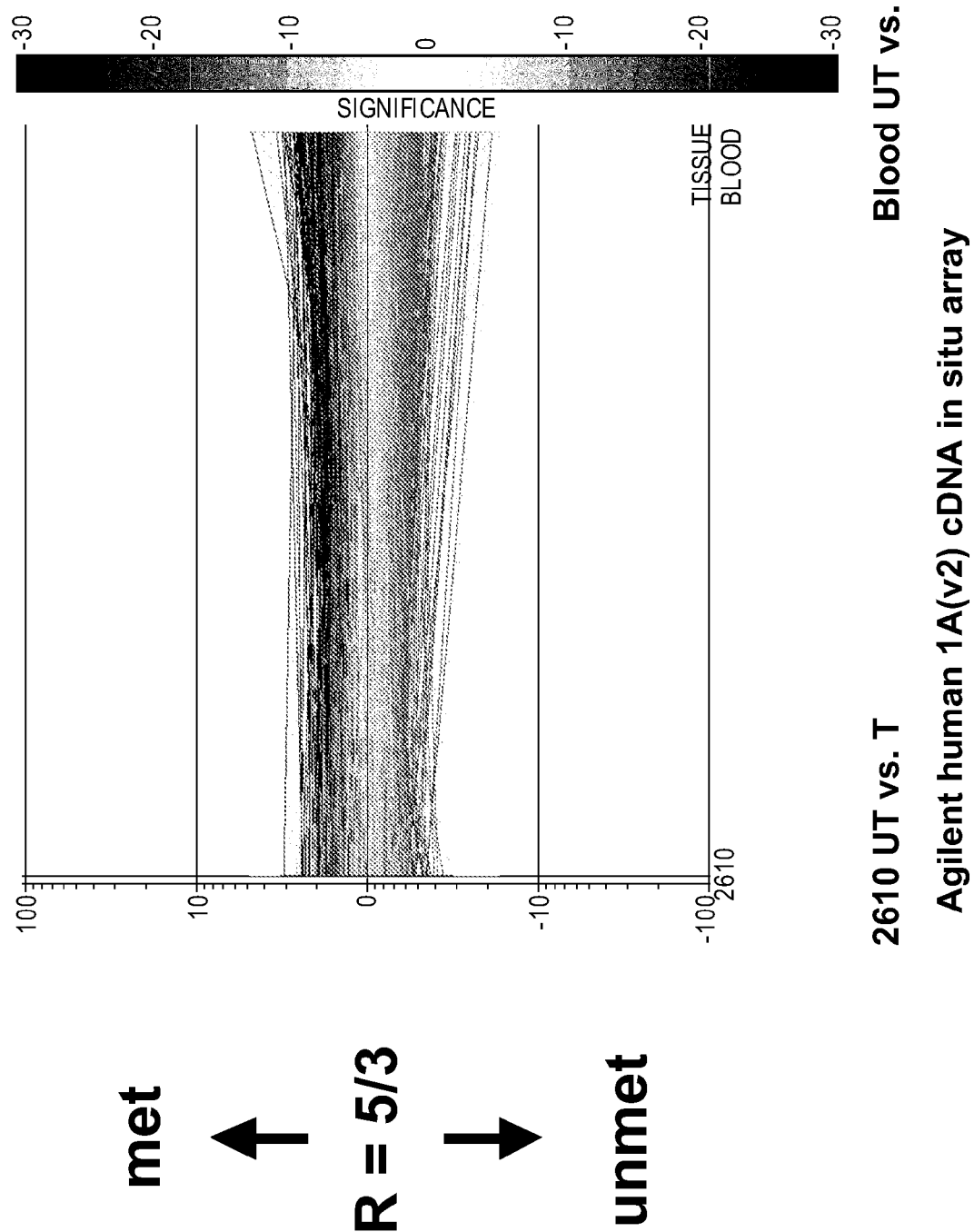
FIG. 8 illustrates the results obtained when the method is used to compare the results from two different samples, in this case ATCC2610 DNA and blood DNA. Microarray hybridization intensity ratios obtained from comparison of undigested amplified ATCC2610 DNA to methylation-dependent digested amplified ATCC2610 DNA are plotted on the left of the graph. Those obtained by the same analysis of blood DNA are plotted on the right of the graph. Data points representing the same feature are connected by a line. The array data demonstrate that the majority of genes do not exhibit altered DNA methylation between blood and the glioma cell line (represented by straight lines). The data also demonstrate that the cancer derived cell line has less overall DNA methylation than the blood sample analyzed (e.g., the distance from high to low methylation ratio is smaller in the cancer cell line). In this way, specific quantified sequences from amplified portions from one sample can be compared to quantified sequences from amplified portions of a second sample and the relative methylation density of a locus can be determined.
Figure 10:
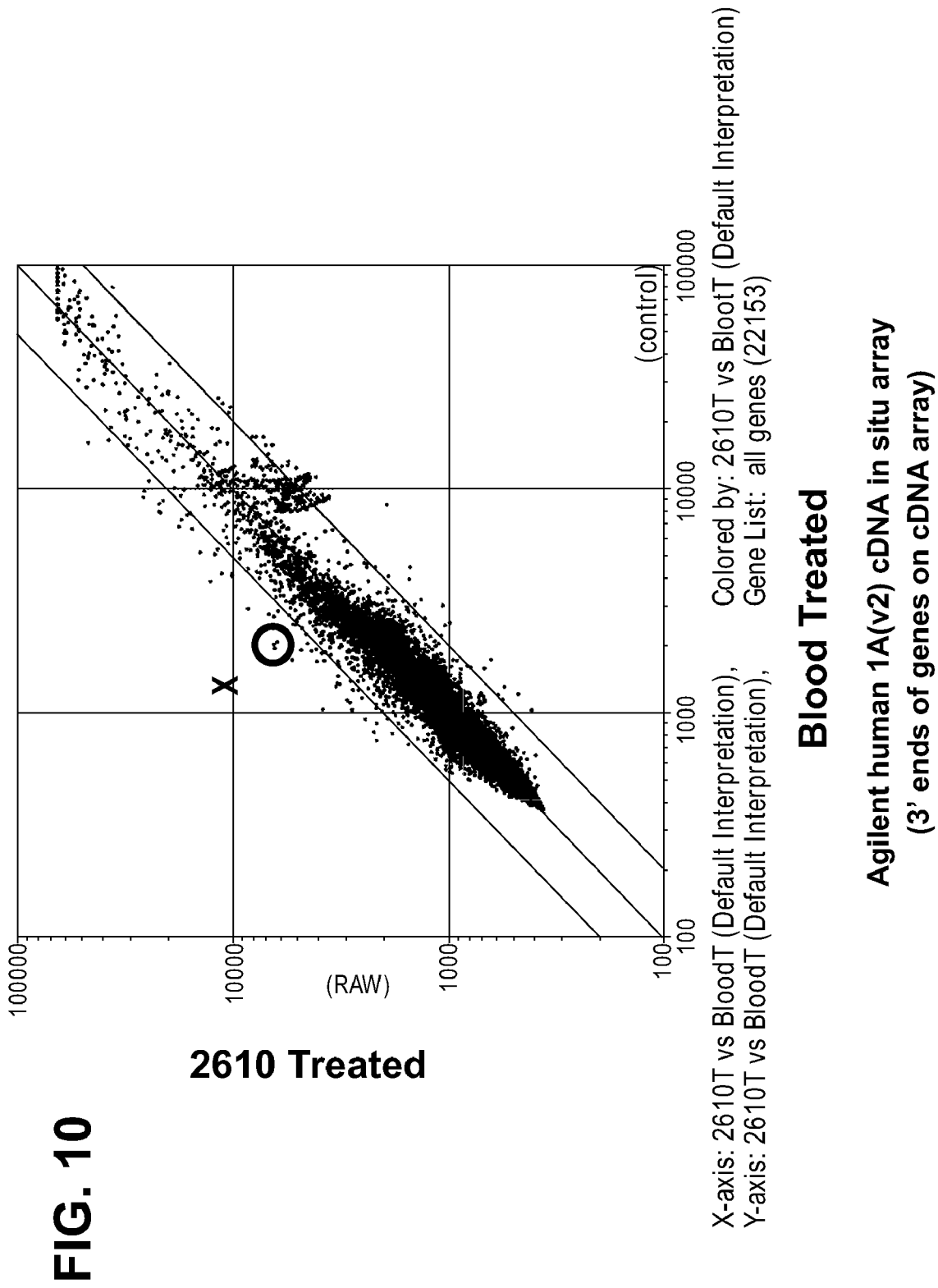
FIG. 10 illustrates the results obtained when portion 3 (i.e., amplified methylation-dependent restriction enzyme treatment) from ATCC2610 DNA was directly analyzed on the array vs. portion 3 from blood DNA. In this analysis, loci that are more methylated in blood will move up and to the left, while genes that are more methylated in the cell line will move down and right. Again a duplicate dye swap experimental construction was employed for the hybridizations. The data demonstrate that gene X (also indicated in FIG. 9) is more methylated in blood DNA than it is in the ATCC2610 genome. In this way, quantified sequences from an amplified portion from one sample can be compared to quantified sequences from an amplified portion of a second sample and the relative methylation density of a locus can be determined.
Figure 11:
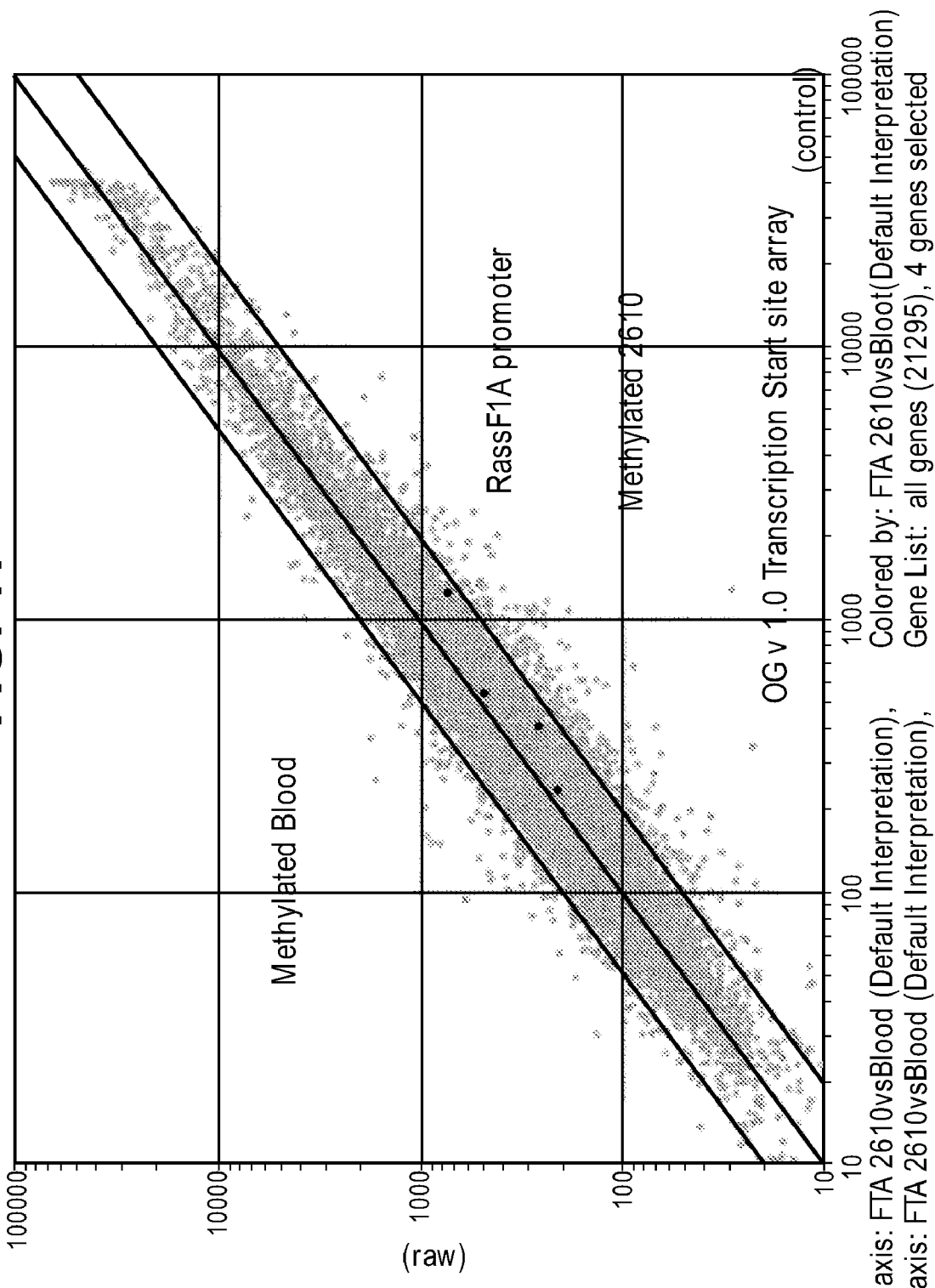
FIG. 11 illustrates the results obtained when portion 3 (amplified methylation-dependent restriction enzyme treatment) from blood DNA is compared to portion 3 from ATCC2610 DNA utilizing a microarray in which the polynucleotide probes represent transcriptional start sites (proximal to promoter sequences). The methylation ratio of all genes is depicted by gray dots. The black dots represent the results obtained from probes representing the RASSF1 A gene. The data demonstrate that the four features targeting the RASSF1 A gene are more methylated in the cell line than in blood. This locus has been demonstrated to be hypermethylated in the majority of primary gliomas and in all glioma cell lines examined to date (Hesson et al., Oncogene. 2004 Mar. 25; 23(13):2408-19.). In this way, quantified sequences from an amplified portion from one sample can be compared to quantified sequences from an amplified portion of a second sample, and the relative methylation density of a locus can be determined.
Figure 12:
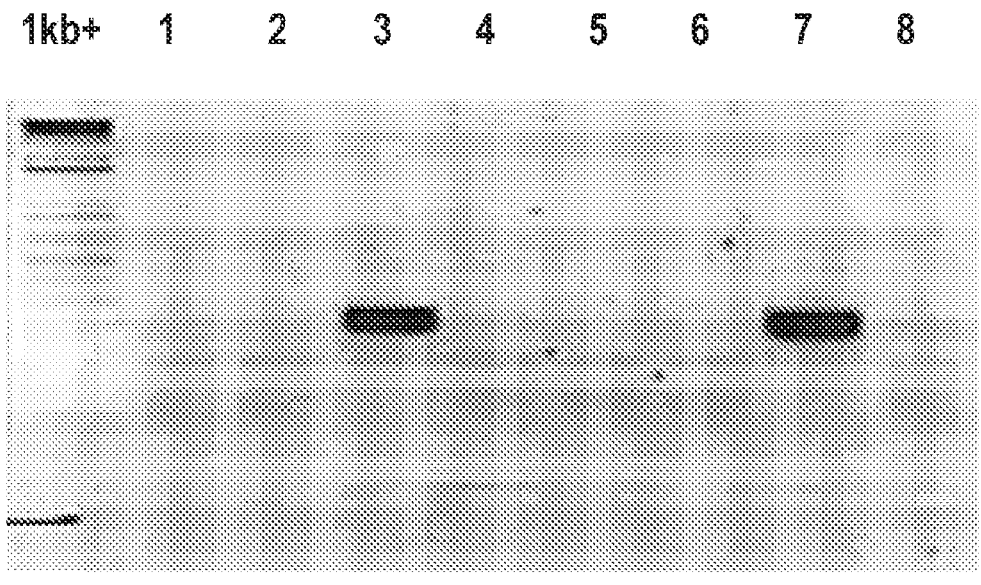
FIG. 12 depicts end point PCR analysis of a specific locus from two portions processed according to the method described in Example 4, along with several "no poly-A tail" controls. After the McrBC digestion step (or mock digestion in the case of samples 1, 3, 5, and 7) the samples in lanes 1-8 underwent whole genome amplification using a poly-T primer, followed by locus specific amplification with locus specific PCR primers. An aliquot of the locus specific PCR reaction was loaded and analyzed with agarose gel electrophoresis. The figure demonstrates whole genome amplification using the poly-A tailing method, and illustrates that a methylation-dependent restriction digested portion fails to amplify a methylated locus in the whole genome amplification step (lanes 4 and 8), while the mock digested portion successfully amplifies a methylated locus in the whole genome amplification step (lanes 3 and 7). In addition, the data also demonstrates that end point PCR analysis of a specific locus is effective in analyzing the content of the amplified portions. In this way, specific quantified sequences from amplified portions from one sample can be compared to each other and the presence of methylation at a locus in a sample can be determined.

D. Digestion of DNA with Restriction Enzymes, and the Introduction of Future Amplification Biases Once sequence tags have been added, or prior to the sequence tags being added in some embodiments, the portions will undergo treatment from a restriction enzyme. In some embodiments, no sequence tags are added. In general, the digestion with one of the restriction enzymes changes the average fragment length of DNA from regions of the genome that differ in DNA methylation density (or in abundance of perfect restriction sites in the case of a methylation-insensitive restriction enzyme), whereby fragments from digested regions will be smaller on average than fragments from undigested regions. This difference in fragment length introduces a bias in a subsequent whole genome amplification step. If the fragments were generated using a restriction enzyme, it is generally preferred that the digestion step be performed with a restriction enzyme that is different than the restriction enzyme used in the fragmenting step. FIGS. 1 through 5 show the embodiments of the present invention, where portions of genomic DNA are being treated with: i) methylation-dependent restriction enzymes, ii) methylation-sensitive restriction enzymes, iii) methylation-insensitive restriction enzymes, iv) a combination of methylation-dependent and methylation-sensitive restriction enzymes, v) not treated (i.e., mock treated) with a restriction enzyme but modified with sequence tags, vi) and not treated with a restriction enzyme and not modified with sequence tags.

In some embodiments, sequence tags are added to at least one end of the sample DNA fragments, generating modified DNA fragments before the amplification step. When digested with a methylation-sensitive restriction enzyme, sequences representing modified DNA fragments that are methylated will be over represented in the final amplification population and sequences representing unmethylated DNA fragments will be under represented in the final amplification population. In this way, an amplification bias in favor of methylated DNA fragments is introduced by the digestion step.

Conversely, when digested with a methylation-dependent restriction enzyme, sequences representing modified DNA fragments that are methylated will be under represented in the final amplification population and sequences representing unmethylated DNA fragments will be over represented in the final amplification population. In this way, an amplification bias in favor of unmethylated DNA fragments is introduced by the digestion step.

Sample DNA can also be digested with a methylation-insensitive restriction enzyme. It is particularly useful to use a methylation-insensitive restriction enzyme that is an isoschizomer with a methylation-sensitive restriction enzyme or a methylation-dependent restriction enzyme used on a different population of sample DNA, because one can compare the number of fragments that survive digestion with the isoschizomeric pair, and one can then determine whether amplification occurred because of a mutation at the isoschizomeric recognition site, or because the isoschizomeric recognition site was in a methylation state incompatible with the methylation-sensitive or methylation dependent restriction enzyme.

When digested with a methylation-insensitive restriction enzyme, sequences representing modified DNA fragments that have sequence changes at certain the recognition sites for the enzyme (or that have imperfect or mutated recognition sites) will be over represented in the final amplification population. Sequences representing DNA fragments that do not have sequence changes at certain recognition sites will be under represented in the final amplification population. In this way, an amplification bias in favor of mutated DNA fragments is introduced by the digesting step.

E. Exonuclease Treatment

In some embodiments, the digestion step is followed by treatment with exonuclease. Exonuclease treatment is a stepwise removal of nucleotides from single- or/and double-stranded DNA. Exonucleases can be specific to either single or double-stranded DNA. Exonucleases preferentially act upon the ends of DNA fragments. One of skill in the art will appreciate that the treatment by exonucleases specific to double- and single strand DNA (for example, ExoIII, Lambda Exo, ExoI, Mung Bean nuclease) could destroy the digested population of DNA leaving the undigested population of DNA intact, providing that the ends of the original DNA fragments (i.e., the DNA fragments before the exonuclease digestion step) are properly protected (e.g., dephosphorylated, having blocking overhangs, or protected by blocking agents, or protected by the addition of sequence tags that are resistant to exonuclease activity). Removal of the digested population of DNA before the amplification step reduces the abundance of sequences representing digested fragments in the final amplification population, and thereby increases the amplification bias introduced by the digestion step.

In some embodiments, the amplification step is followed by treatment with an exonuclease. For example, treatment following amplification with ExonucleaseI will destroy the accumulated linear amplification products and can improve sensitivity in the quantifying step because in some cases, linear amplification products can be produced from digested modified DNA fragments.

F. Amplification of Digested or Undigested of Sample DNA Populations

1. Random and Universal Priming Mediated Amplification

Amplification of digested or undigested sample DNA populations can be driven by random priming of DNA template sequences, or by the universal priming of added DNA sequence tags.

If random primers are used to amplify the DNA populations, the addition of defined sequence tags is not required. In some embodiments, short random primers are added along with amplification reagents (e.g., polymerase, dNTPs, and an appropriate buffer) and a simple bias is observed. Strands from longer DNA fragments from the DNA sample are more likely to match (i.e., have complementary sequences of) random primers of a given length than strands from shorter DNA fragments. Random priming kinetics can be altered in two ways: 1) by varying primer length (i.e., long primers will anneal less frequently than short primers), or 2) by varying DNA fragment length (i.e., primers will anneal more frequently to the longer fragments). Because DNA fragment length can be impacted by restriction enzyme digestion, digesting DNA with methylation sensing enzymes will introduce an amplification bias in either unmethylated or methylated sequences in the sample. For example, the sequences that have less methylation are more likely to be digested by methylation sensitive restriction enzymes, and will on average be shorter than sequences that have more methylation. Conversely, the sequences that have less methylation are less likely to be digested less by methylation dependent restriction enzymes, and on average will be longer than sequences that have more methylation. Longer sequences will amplify more efficiently with random primers than shorter sequences, and will comprise a greater percentage of an amplified population of sequences than they did in the original unamplified population.

If universal primers are used to amplify the DNA populations, defined sequence tags have generally been added to the DNA fragments. In some embodiments, polynucleotide primers with a universal sequence matching the sequence of the sequence tags are used in an exponential amplification reaction, such as PCR. In these embodiments, intact fragments with sequence tags at both ends will amplify exponentially, while digested fragments having only one sequence tag will amplify linearly. In the final amplification population, exponentially amplified products with sequences representing uncleaved fragments will be present in higher concentration than linearly amplified products with sequences representing the cleaved population of fragments.

For embodiments employing linear amplification methods, digestion with restriction enzymes creates cut and uncut (full-length) fragments. Probes used to detect the linear amplification products of the cut and uncut fragments will more likely detect the uncut fragments compared to the cut fragments as the entire cut fragment will not be amplified.

2. Methods of Amplification

Several methods of whole genome amplification are known to those skilled in the art. The polymerase chain reaction (PCR), branched chain or strand displacement amplification technologies, transcription coupled or cRNA amplification (or promoter or transcription driven amplification), linear amplification, nick translation, or any amplification method can be used so long as the method preferentially amplifies one subportion (e.g., digested or undigested DNA fragments) more efficiently than the other.

G. Detecting Amplification Products Containing a Specific Sequence

Specific sequences in the final amplification population can be further evaluated, detected, cloned, sequenced, and the like, either in solution or after binding to a solid support, by any method usually applied to the detection of specific DNA sequences.

1. Detecting a Specific Sequence in DNA Populations with a Polynucleotide Attached to a Solid Support Specific sequences in the final amplified population that match the sequence of DNA which remained undigested by the restriction enzymes may be hybridized to one or a plurality of polynucleotides (e.g., under conditions in which the amplified DNA binds to its complementary sequence). Hybridization of the amplified DNA sequences to the polynucleotides provides information regarding whether a particular polynucleotide is methylated or not and can provide information regarding the amount of methylation (e.g., the proportion of methylated or unmethylated DNA sequences) in the sample.

One of skill in the art will appreciate that hybridization of the amplified DNA sequences to polynucleotides can be accomplished using any means known in the art. In some embodiments, the polynucleotides are linked to a solid support. Methods of hybridizing nucleic acid sequences to a polynucleotide on a solid support (e.g., a bead or a microarray) and detecting the bound sequences are described in, e.g., Bowtell and Sambrook, *DNA Microarrays: A Molecular Cloning Manual*. (2003).

To simultaneously quantify a large number of specific DNA sequences in a population of DNA fragments, it can be convenient to label the DNA population with a fluorescent label, and hybridize the labeled DNA to a microarray or other addressable array of polynucleotides (or probes). The number of different quantifying polynucleotide probes can be, e.g., at least about 2, 5, 10, 20, 50, 100, 500, 1,000, 10,000, 100,000 or more. One of skill in the art will appreciate that polynucleotides can be designed to hybridize to any target sequence of interest including, but not limited to, genomic DNA, cDNA, unmethylated DNA, methylated DNA, and the like.

When the same polynucleotide is used to quantify specific sequences in more than one population of DNA, a comparison can be made between the relative concentrations of DNA fragments containing the specific sequence that hybridizes to the polynucleotide in both populations. These relative concentrations can be interpreted in terms of a methylation profile.

In cases where only one label (i.e. Cy3) is used to label DNA, at least two different target DNA samples are prepared and labeled with the same labeling moieties. The two samples are kept separate and are each hybridized to a separate microarray. The microarrays are then examined under conditions in which the emissions from the label are detectable, and the results from the two arrays are compared.

In cases where differentially labeled targets are used (e.g., more than one label), at least two different target DNA samples are prepared and labeled with different labeling moieties. The mixture of the two or more labeled DNA samples is added to a single microarray. The microarray is then examined under conditions in which the emissions from each of the two or more different labels are individually detectable, and the results from the two labels are compared.

In some embodiments, the labels are fluorescent labels with distinguishable emission spectra, such as a lissamine-conjugated nucleotide analog and a fluorescein conjugated nucleotide analog. In another embodiment, Cy3/Cy5 fluorophores (Amersham Pharmacia Biotech) are employed. For instance, for microarray applications, it can be convenient to use fluorescent labels (e.g., Cy3 or Cy5) that are readily detected. However, those of skill in the art will recognize that any type of detectable label can be employed (e.g., radioactive, fluorescent, enzymatic, or other methods known to those of skill in the art).

After hybridization, the microarray is washed to remove non-hybridized nucleic acids, and complex formation between the hybridizable array elements (i.e., probes) and the target (i.e., labeled moiety) is detected. Methods for detecting complex formation are well known to those skilled in the art. As discussed above, in some embodiments, the target polynucleotides are labeled with a fluorescent label, and measurement of levels and patterns of fluorescence indicative of complex formation is accomplished by fluorescence microscopy, such as confocal fluorescence microscopy. An argon ion laser excites the fluorescent label, emissions are directed to a photomultiplier, and the amount of emitted light is detected and quantified. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance of each hybridized target polynucleotide.

In a differential hybridization experiment, fluorescent signals can be detected separately with different photomultipliers set to detect specific wavelengths. The relative abundances/expression levels of the differentially-labeled target polynucleotides are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray or from the intensity of hybridization of total genomic DNA.

2. Detecting a Specific Sequence in DNA Populations with a Polynucleotide Used in Additional Amplification Reactions In some embodiments, the presence and quantity of specific sequences in the final amplified population can be determined by an additional amplification of the specific locus from the final amplified population. For example, PCR reactions can be designed in which specific amplification primers flank a particular locus of interest. Amplification occurs when the locus comprising the two primers is represented in the final amplification population. Amplification of a DNA locus using reactions is well known (see U.S. Pat. Nos. 4,683,195 and 4,683,202; PCR PROTOCOLS: A GUIDE to METHODS AND APPLICATIONS (Innis et al., eds, 1990)). Typically, PCR is used to amplify DNA templates. Additionally, oligomer restriction (Saiki, et al., Bio/Technology 3:1008-1012 (1985)), allele-specific oligonucleotide (ASO) probe analysis (Conner, et al., PNAS USA 80:278 (1983)), oligonucleotide ligation assays (OLAs) (Landegren, et al., Science 241:1077, (1988)), and other DNA amplification methods can be employed to quantify a specific sequence in the final amplification population. Molecular techniques for DNA analysis have been reviewed (Landegren, et al., Science 242:229-237 (1988)).

Quantitative amplification methods (e.g., quantitative PCR or quantitative linear amplification) can also be used to quantify the amount of a specific sequence in the final amplified population, which will correlate to the amount of intact DNA matching the same sequence following restriction digestion of the DNA sample. Methods of quantitative amplification are disclosed in, e.g., U.S. Pat. Nos. 6,180,349; 6,033,854; and 5,972,602, as well as in, e.g., Gibson et al., Genome Research 6:995-1001 (1996); DeGraves, et al., Biotechniques 34(1): 106-10, 112-5 (2003); Delman B, et al., Mol Biotechnol. 20(2):163-79 (2002). Amplifications may be monitored in "real time."

In general, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. Genome Methods 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., PNAS USA 88: 7276-7280 (1991); Lee et al., Nucleic Acids Res. 21: 3761-3766 (1993)). This assay detects the accumulation of a specific PCR product by hybridization and cleavage of a doubly labeled fluorogenic probe (the "TaqMan™" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, Nature Biotech. 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, Nature Biotechnol. 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., Nature Biotechnology 17:804-807, 1999, and U.S. Pat. No. 6,326,145), Sunrise™ (or Amplifluor™) probes (e.g., Nazarenko et al., Nuc. Acids Res. 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREENT™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

Quantitation of a specific amplified product at the end of an amplification reaction (i.e., end-point PCR) can be employed to quantify the sequences in the final amplified population that match the sequence of DNA which remained undigested by the restriction enzymes. The end-point PCR analysis will have to be employed under conditions in which the reaction can be analyzed before the reactant nears depletion for a quantitative comparison. Most typically this is done through a comparison of reaction products following a limited number of cycles. For example, a reaction is allowed to cycle 10 times, 15 times, 20 times or 30 times. The quantities of end point PCR products can be compared to each other and an analysis of sequences from the differential enzyme treatments of the DNA sample can be made.

3. Detecting a Specific Sequence in the DNA Populations with a Polynucleotide Used in Hybrid Capture In some embodiments, nucleic acid hybrid capture assays can be used to detect the presence and quantity of a specific sequence in the final amplified population that match the sequence of DNA which remained undigested by the restriction enzymes. Following whole genome amplification, RNA probes which specifically hybridize to DNA sequences of interest are combined with the DNA to form RNA:DNA hybrids. Antibodies that bind to RNA:DNA hybrids are then used to detect the presence of the hybrids and therefore, the presence and amount of uncut DNA. DNA fragments that are restricted in a window of sequence that is complementary to the RNA probe hybridize less efficiently to the RNA probe than do DNA fragments that remain intact in the window of sequence being monitored. The amount of hybridization allows one to quantify specific sequences in the final amplification population, and the quantity of DNA methylation can be inferred directly from the quantity of sequences representing intact DNA from different restriction enzyme treatments of the DNA sample (i.e., methylation-sensitive and/or methylation-dependent restriction enzyme treatments). One of skill in the art will recognize that if cRNA amplification was used then the polynucleotide used to quantify could be DNA, thus allowing antibody based detection of RNA:DNA hybrids.

Methods of detecting RNA:DNA hybrids using antibodies are known in the art and are described in, e.g., Van Der Pol et al., *J. Clin. Microbiol.* 40(10): 3558 (2002); Federschneider et al., *Am. J. Obstet. Gynecol.* 191(3):757 (2004); Pretet et al., *J. Clin. Virol.* 31(2):140-7 (2004); Giovannelli et al., *J. Clin. Microbiol.* 42(8):3861 (2004); Masumoto et al., *Gynecol. Oncol.* 94(2):509-14 (2004); Nonogaki et al., *Acta Cytol.* 48(4):514 (2004); Negri et al., *Am. J. Clin. Pathol.* 122(1):90 (2004); Sarian et al., *Gynecol. Oncol.* 94(1):181 (2004); Oliveira et al., *Diagn. Cytopathol.* 31(1):19 (2004); Rowe et al., *Diagn. Cytopathol.* 30(6):426 (2004); Clavel et al., *Br. J. Cancer* 90(9):1803-8 (2004); Schiller et al., *Am. J. Clin. Pathol.* 121(4):537 (2004); Arbyn et al., *J. Natl. Cancer Inst.* 96(4):280 (2004); Syrjanen et al., *J. Clin. Microbiol.* 2004 February; 42(2):505 (2004); Lin et al., *J. Clin. Microbiol.* 42(1):366 (2004); Guyot et al., *BMC Infect. Dis.* 25; 3(1):23 (2003); Kim et al., *Gynecol. Oncol.* 89(2):210-7 (2003); Negri et al., *Am J Surg Pathol.* 27(2):187 (2003); Vince et al., *J. Clin. Virol. Suppl* 3:S109 (2002); Poljak et al., *J. Clin. Virol. Suppl* 3:S89 (2002). In some cases, the antibodies are labeled with a detectable label (e.g., an enzymatic label, an isotope, or a fluorescent label) to facilitate detection. Alternatively, the antibody:nucleic acid complex may be further contacted with a secondary antibody labeled with a detectable label. For a review of suitable immunological and immunoassay procedures, see, e.g., Harlow & Lane, ANTIBODIES, A LABORATORY MANUAL, Cold Spring Harbor Publication, New York (1988); *Basic and Clinical Immunology* (Stites & Terr eds., 7$^{th}$ ed. 1991); U.S. Pat. Nos. 4,366,241; 4,376,110; 4,517,288; and 4,837,168); Methods in Cell Biology: Antibodies in Cell Biology, volume 37 (Asai, ed. 1993).

Monoclonal, polyclonal antibodies, or mixtures thereof may be used to bind the RNA:DNA hybrids. Detection of RNA:DNA hybrids using monoclonal antibodies is described in, e.g., U.S. Pat. Nos. 4,732,847 and 4,833,084. Detection of RNA:DNA hybrids using polyclonal antibodies is described in, e.g., U.S. Pat. No. 6,686,151. The polyclonal or monoclonal antibodies may be generated with specific binding properties. For example, monoclonal or polyclonal antibodies that specifically bind to shorter (e.g., less than 20 base pairs) or longer (e.g., more than 100 base pairs) RNA:DNA hybrids may be generated. In addition, monoclonal or polyclonal antibodies may be produced that are either more or less sensitive to mismatches within the RNA:DNA hybrid.

4. Using a Polynucleotide to Detect a Specific Sequence in DNA Populations Treated with an Agent that Convert Unmethylated Cytosines In some embodiments, following or preceding digestion with the restriction enzyme, the DNA sample is treated with an agent that modifies unmethylated cytosines. For example, sodium bisulfite is added to the DNA, thereby converting unmethylated cytosines to uracil, leaving the methylated cytosines intact. In these embodiments, a specific sequence in the final amplified population that matches the sequence of DNA which remained undigested by the restriction enzymes may also be quantified using a polynucleotide that hybridizes to a specific treated DNA sequence. In some embodiments, a polynucleotide is designed to recognize a sequence that is typically not methylated. In some embodiments, polynucleotides are designed to recognize a sequence that is typically methylated. In this case, a polynucleotide can be designed to recognize the treated methylated or treated unmethylated sequence. One or more primers are designed to distinguish between the methylated and unmethylated sequences that have been treated with sodium bisulfite. For example, primers complementary to the bisulfite-treated methylated sequence will contain guanosines, which are complementary to endogenous cytosines. Primers complementary to the bisulfite-treated unmethylated sequence will contain adenosines, which are complementary to the uracil, the conversion product of unmethylated cytosine. Preferably, nucleotides that distinguish between the treated methylated and treated unmethylated sequences will be at or near the 3' end of the primers. Variations of methods using sodium bisulfite-based PCR are described in, e.g., Herman et al., *PNAS USA* 93:9821-9826 (1996); U.S. Pat. Nos. 5,786,146 and 6,200,756. The quantifying polynucleotide can be hybridized to specific sequences in an additional round of PCR, or the polynucleotide can be used to directly detect specific sequences in the final amplification population. Polynucleotides can also be designed to hybridize to recognize regions of DNA sequence that can not be methylated by the host organism. In this case, the polynucleotides are designed to recognize the treated unmethylated sequence.

H. Comparisons Allow for the Detection of Methylation at a Locus within a Nucleic Acid Population Methods of the invention provide for using the same polynucleotide sequence to quantify a specific sequences in more than one population of DNA, a comparison can be made between the relative concentrations of DNA fragments containing the specific sequence that hybridizes to the polynucleotide in both populations. To the extent that the populations are biased representations of DNA sequence present in the original sample DNA population, relative concentrations can be interpreted in terms of a methylation profile.

Methods of the invention may comprise comparing the presence or absence or amounts of intact DNA following restriction of a sample divided into at least two portions, wherein the portions are treated with different restriction enzymes. While the following discussion refers to a "first portion", a "second portion", a "third portion", etc., it is understood that the designations are used only for the purposes of identifying the various fragments and are not intended to indicate either sequential order or the total number of comparisons made. For example, the "first portion" and the "fourth portion" can be compared without determining the "second portion" or the "third portion".

In many embodiments, a first portion is contacted with a methylation-dependent restriction enzyme (producing intact unmethylated DNA and fragmented methylated DNA) and a second portion is contacted with a methylation-sensitive restriction enzyme (producing intact methylated DNA and fragmented unmethylated DNA). The portions are then amplified generating final amplification populations. Specific sequences are quantified in the amplification populations of each portion and the number of intact copies of the locus from each portion are computed and compared. If a specific sequence is abundant in one population, and rare in the other, then one can infer the methylation state of the original DNA population.

In some embodiments, a third portion of nucleic acids comprising the locus is not digested with a restriction enzyme, the portion is amplified, and at least one specific sequence is quantified in the final amplification population to provide an analysis of the total number of intact copies of a locus in a sample. The total number of the intact copies of the locus can be compared to the number of methylated loci and/or the number of unmethylated loci to verify that the number of methylated loci and unmethylated loci are equal to the total number of loci.

In further embodiments, a fourth portion of nucleic acids comprising the locus is digested with both the methylation-sensitive restriction enzyme and the methylation-dependent restriction enzyme, the portion is amplified, and at least one specific sequence is quantified in the final amplification population, and any intact loci are quantified. The total number of intact loci remaining after the double digestion can be compared to the number of methylated copies of the locus, unmethylated copies of the locus, and/or total copies of the locus to verify that the number of methylated copies and unmethylated copies are equal to the total number of copies and to verify that the digestion of the methylation-sensitive and methylation-dependent restriction enzymes is complete.

In even further embodiments, a fifth portion of nucleic acids comprising the locus is digested with a methylation-insensitive restriction enzyme (i.e., insensitive to methylation of either an adenosine or a cytosine residue at its recognition sequence), the portion is amplified, and at least one specific sequence is quantified in the final amplification population, and any intact copies of the locus are detected. The total number of intact copies remaining after digestion can be compared to the number of methylated copies, unmethylated copies, and/or total copies to verify that the digestion of the other methylation-sensitive and methylation-dependent restriction enzymes is complete; and/or to identify mutations in copies of the locus that affect the recognition site of the methylation-sensitive and methylation-dependent restriction enzymes.

In even further embodiments, a sixth portion of nucleic acids comprising the locus is not digested with a restriction enzyme, the portion is not amplified, and at least one specific sequence is quantified in the undigested, unamplified DNA sample to provide an analysis of the total number of intact copies of a locus in a sample. The total number of the intact copies of the locus can be compared to the number of methylated loci and/or the number of unmethylated loci to verify that the number of methylated loci and unmethylated loci are equal to the total number of loci.

Thus, a comparison of any or all of at least six separate nucleic acid populations can be made:

(1) an untreated or mock treated population where virtually all of the copies of the locus remain intact, are efficiently amplified and are abundantly represented in the final amplification population;

(2) a population treated with a methylation-dependent restriction enzyme where virtually all of the unmethylated copies of the locus remain intact, are efficiently amplified and are abundantly represented in the final amplification population;

(3) a population treated with a methylation-sensitive restriction enzyme where virtually all of the methylated copies of the locus remain intact, are efficiently amplified and are abundantly represented in the final amplification population;

(4) a population treated with both a methylation-dependent restriction enzyme and a methylation-sensitive restriction enzyme which contains no or few intact copies of the locus, however, those which remain intact are efficiently amplified and are represented in the final amplification population;

(5) a population treated with a methylation insensitive restriction enzyme which contains no or few intact copies of the locus, except copies of the locus that are mutated at the recognition site of the restriction enzyme, which are then efficiently amplified and are represented in the final amplification population; and (6) an untreated or mock treated population, which remains unamplified, where virtually all of the copies of the locus remain intact and are represented in the DNA sample.

In some embodiments, the samples are divided into equal portions, each of which contains all of the sequences present in the sample. In some embodiments, the samples may be divided into parts that do not contain all of the sequences present in the sample. By comparing results from the quantification of the final amplification populations from the different combinations of restriction digests, the number of methylated and unmethylated copies of the locus of interest can be determined. Any of the above populations can thus be compared to any other population. For example, populations (1) and (2) can be compared with one another; or either population (1) or (2) can be compared with another population, e.g., population (4).

FIGS. 1 through 5 show the various comparisons that may be made.

In some embodiments, the DNA sample may be digested with both methylation-sensitive and methylation-dependent restriction enzymes. The sample may be digested with a respective restriction enzyme in a certain order, e.g., to first digest with a particular class of methylation-sensing enzymes, e.g., methylation-sensitive enzymes. Similarly, in some embodiments, a double digest (e.g., a simultaneous digest with more than one enzyme) may be performed.

In some embodiments, the nucleic acid may be obtained from a sample comprising a mixed population of members having different methylation profiles. For example, a biological sample may comprise at least one cell type with little or no methylation at a locus of interest and at least one cell type that is methylated at the locus. The proportion of the population constituting methylated or unmethylated loci can be assessed by comparing the amount of undigested loci in a single-digested aliquot treated with only methylation-sensitive or methylation-dependent restriction enzyme(s) to the amount of undigested DNA in an aliquot treated with both methylation-sensitive and methylation-dependent restriction enzymes. As used in this context, a "single" digest may, in practice, be performed using more than one enzyme that is methylation-sensitive, or more than one enzyme that is methylation-dependent, whether used sequentially or simultaneously.

For example, an aliquot that is digested with more than one methylation-sensitive restriction enzyme, but no methylation-dependent restriction enzymes is considered a "single" digest. A "double" digest is considered to be an aliquot that has been treated using both methylation-sensitive and methylation-dependent restriction enzymes, whether used sequentially or simultaneously, regardless of the number of methylation-sensitive and methylation-dependent restriction enzymes employed.

The amount of undigested DNA in a single digest relative to a double digest and the total number of copies of the locus in the sample is indicative of the proportion of cells that contain unmethylated vs. methylated DNA at a locus of interest. Furthermore, such an analysis can serve as a control for the efficacy of the single digest, e.g., the presence of a detectable change in the amount of undigested DNA in the double digest compared to the amount in the single digest with a methylation-sensitive restriction enzyme is an indication that the single digest went to completion.

One of skill in the art will appreciate that, by selecting appropriate combinations of restriction enzymes (e.g., methylation-sensitive, methylation-dependent, and methylation-insensitive restriction enzymes), the methods of the invention can be used to determine cytosine methylation or adenosine methylation at a particular locus based on, e.g., the recognition sequence of the restriction enzyme. For example, by digesting a first portion of nucleic acids comprising a locus of interest with a methylation-sensitive restriction enzyme which fails to cut when a methylated cytosine residue is in its recognition sequence (e.g., Hha 1), and digesting a second portion of nucleic acids comprising a locus of interest with a methylation-dependent restriction enzyme which cuts only if its recognition sequence comprises a methylated cytosine (e.g., McrBC), the cytosine methylation of a particular locus may be determined.

Likewise, by digesting a first portion of nucleic acids comprising a locus of interest with a methylation-sensitive restriction enzyme which fails to cut when an adenosine residue is methylated in its recognition sequence (e.g., Mbo I), and digesting a second portion of nucleic acids comprising a locus of interest with a methylation-dependent restriction enzyme which cuts in the presence of methylated adenosines in its recognition sequence (e.g., Dpn I), the adenosine methylation of a particular locus may be determined. In some embodiments, all four sets of digestions are conducted in parallel for both adenosine methylation and cytosine methylation to simultaneously determine the presence of adenosine methylation and cytosine methylation at a particular locus.

In addition, restriction enzymes that are sensitive to either methylated cytosine or methylated adenosine can be used in the methods of the invention to provide populations of cytosine methylated loci and adenosine methylated loci for comparison.

In some embodiments, the nucleic acid portions are treated with an agent, such as sodium bisulfite, that modifies (or converts) a particular unmethylated base prior to treatment with restriction enzymes. The nucleic acids can then be treated and quantified through an amplification using at least one primer that distinguishes between protected methylated and converted unmethylated nucleotides. The amplified portions are then compared to determine relative methylation. Certain quantitative amplification technologies employ one or more detection probes that are distinct from the amplification primers. These detection probes can also be designed to discriminate between protected methylated and converted unmethylated DNA.

This invention relies on routine techniques in the field of recombinant genetics. For example, methods of isolating genomic DNA, digesting DNA with restriction enzymes, ligating polynucleotide sequences, detecting amplified and unamplified DNA, and sequencing nucleic acids are \veil known in the art. Basic texts disclosing the general methods of use in this invention include Sambrook et al., MOLECULAR CLONING, A LABORATORY MANUAL (3rd ed. 2001); Kriegler, GENE TRANSFER AND EXPRESSION: A LABORATORY MANUAL (1990); and CURRENT PROTOCOLS IN MOLECULAR BIOLOGY (Ausubel et al., eds., 2001)).

I. Detection of Methylation Differences Between Samples and at Specific Loci

The methods of the invention can be used to detect differences in methylation between nucleic acid samples (e.g., DNA or genomic DNA) and/or at specific loci. In some embodiments, the methods can be used to analyze a sample of DNA where all copies of a genomic DNA locus have an identical methylation pattern. In some embodiments, the DNA sample is a mixture of DNA comprising alleles of a DNA locus in which some alleles are more methylated than others. In some embodiments, a DNA sample contains DNA from two or more different cell types, wherein each cell type has a different methylation density at a particular locus (e.g., a cell from a tissue suspected of being diseased and a cell from a non-diseased tissue sample). For example, at some loci, neoplastic cells have different methylation densities compared to normal cells. If a tissue, body fluid, or secretion contains DNA from both normal and neoplastic cells, the DNA sample from the tissue, body fluid, or secretion will comprise a heterogeneous mixture of differentially methylated alleles. In this case, at a given locus, one set of alleles within the DNA (e.g., those derived from neoplastic cells in the sample) will have a different methylation density than the other set of alleles (e.g., those derived from normal cells).

In cases where a particular phenotype or disease is to be detected, DNA samples should be prepared from a tissue of interest, or as appropriate, from blood. For example, DNA can be prepared from biopsy tissue to detect the methylation state of a particular locus associated with cancer. The nucleic acid-containing specimen used for detection of methylated loci (see, e.g., Ausubel et al., CURRENT PROTOCOLS IN MOLECULAR BIOLOGY (1995 supplement)) may be from any source including brain, colon, urogenital, hematopoietic, thymus, testis, ovarian, uterine, prostate, breast, colon, lung and renal tissue and may be extracted by a variety of techniques such as that described by Ausubel et al., CURRENT PROTOCOLS IN MOLECULAR BIOLOGY (1995) or Sambrook et al., MOLECULAR CLONING, A LABORATORY MANUAL (3rd ed. 2001).

Detection and identification of loci of altered methylation (compared to normal cells) in DNA samples can indicate that at least some of the cells from which the sample was derived are diseased. Such diseases include but are not limited to, e.g., low grade astrocytoma, anaplastic astrocytoma, glioblastoma, medulloblastoma, colon cancer, liver cancer, lung cancer, renal cancer, leukemia (e.g., acute lymphocytic leukemia, chronic lymphocytic leukemia, acute myeloid leukemia, chronic myeloid leukemia), lymphoma, breast cancer, prostate cancer, cervical cancer, endometrial cancer, neuroblastoma, cancer of the oral cavity (e.g., tongue, mouth, pharynx), esophageal cancer, stomach cancer, cancer of the small intestine, rectal cancer, anal cancer, cancer of the anal canal and anorectum, cancer of the intrahepatic bile duct, gallbladder cancer, biliary cancer, pancreatic cancer, bone cancer, cancer of the joints, skin cancer (e.g., melanoma, non-epithelial cancer, basal cell carcinoma, squamous cell carcinoma), soft tissue cancers, uterine cancer, ovarian cancer, vulval cancer, vaginal cancer, urinary cancer, cancer of the ureter, cancer of the eye, head and neck cancer, non-Hodgkin lymphoma, Hodgkin lymphoma, multiple myeloma, brain cancer, cancer of the nervous system. Identification of altered methylation profiles is also useful for detection and diagnosis of loss of genomic imprinting, fragile X syndrome and X-chromosome inactivation.

Specific loci that are suitable for analysis using the methods of the invention are described in, e.g., Costello and Plass, *J. Med. Genet.* 38:285-303 (2001) and Jones and Baylin, *Nature. Rev.* 3:415-428 (2002) and are set forth in Table 1 below.

TABLE 1

Examples of Genes Exhibiting Hypermethylation in Cancer

| Gene | Effect of loss of function in tumor development | Tumor types |
|---|---|---|
| Rb | Loss of cell-cycle control | Retinoblastoma |
| MLH1 | Increased mutation rate, drug resistance | Colon, ovarian, endometrial, gastric |
| BRCA1 | Genomic instability | Breast, ovarian |
| E-CAD | Increased cell motility | Breast, gastric, lung, prostate, colon, leukemia |
| APC | Aberrant cell transduction | Breast, lung, colon, gastric, esophageal, pancreatic, hepatocellular |
| p16 | Loss of cell-cycle control | Most tumor types |
| VHL | Altered protein degradation | Clear-cell renal cell carcinoma |
| p73 | Loss of cell-cycle control | Leukemia, lymphoma, ovarian |
| RASSF1A | Aberrant cell transduction | Lung, breast, ovarian, kidney, nasopharyngeal |
| p15 | Loss of cell-cycle control | Leukemia, lymphoma, gastric, squamous cell carcinoma, hepatocellular |
| GSTP1 | Increased DNA damage | Prostate |
| DAPK | Reduced apoptosis | Lymphoma, lung |
| MGMT | Increased mutation rate | Colon, lung, brain, esophageal, gastric |
| P14ARF | Loss of cell cycle control | Melanoma, non-melanoma skin cancer, pancreatic, breast, head and neck, lung, mesothelioma, neurofibromatosis, colon, soft tissue sarcoma, bladder, Hodgkin's, Ewing's sarcoma, Wilm's tumor, osteosarcoma, rhabdomyosarcoma |
| ATM | Defective DNA repair | Leukemia, lymphoma |
| CDKN2B | Loss of cell cycle control | Breast, ovarian, prostate |
| FHIT | Defective DNA repair | Lung, pancreas, stomach, kidney, cervix, breast |
| MSH2 | Defective DNA repair | Colon |
| NF1/2 | Loss of cell cycle control | Neurofibroma |
| PTCH | Loss of cell cycle control | Skin, basal and squamous cell carcinomas, brain |
| PTEN | Loss of cell cycle control | Breast, thyroid, skin, head and neck, endometrial |
| SMAD4 | Loss of cell cycle control | Pancreas, colon |
| SMARCA3/B1 | Loss of cell cycle control | Colon |
| STK11 | Loss of cell cycle control | Melanoma, gastrointestinal |
| TIMP3 | Disruption of cellular matrix | Uterus, breast, colon, brain, kidney |
| TP53 | Loss of cell cycle control; reduced apoptosis | Colon, prostate, breast, gall bladder, bile duct, |
| BCL2 | Loss of cell cycle control; reduced apoptosis | Lymphoma, breast |
| OBCAM | Loss of cell cycle | Ovarian |
| GATA4 | Transcriptional silencing of downstream genes | Colorectal, gastric, ovary |
| GATA5 | Transcriptional silencing of downstream genes | Colorectal, gastric, ovary |
| HIC1 | Loss of cell cycle control | Epithelium, lymphoma, sarcoma |

Abbreviations: APC, adenomatous polyposis coli; BRCA1, breast cancer 1; DAPK, death-associated protein kinase; E-cad, epithelial cadherin; GSTP1 glutathione S-transferase π1; MLH1, MutL homologue 1, MGMT, O(6)-methylguanine-DNA methyltransferase; p15, $p15^{INK4b}$; p16, $p16^{INK4}$; p73, p73; Rb, retinoblastoma; RASSF1a, Ras association domain family 1A; VHL, von Hippel-Lindau; ATM, ataxia telangiectasia mutated; CDKN2, cyclin dependent kinase inhibitor; FHIT, fragile histidine triad; MSH2, mutS homologue 2; NF1/2, neurofibromin 1/2; PTCH, patched homologue; PTEN, phosphatase and tensin homologue; SMAD4, mothers against decapentaplegic homologue 4; SMARCA3/B1, SWI/SNF-related, matrix-associated, actin-dependent regulator of chromatin, subfamily A, member 3/subfamily B, member 1; STK11, serine/threonine kinase 11; TIMP3, tissue inhibitor of metalloproteinase 3; Bcl-2m B-call CLL/Lymphoma 2; OBCAM, opoid-binding cell adhesion molecule; GATA, globin transcription factor; HIC1, hypermethylated in cancer.

In some embodiments, the methylation of sample from the same individual is determined over a period of time, e.g., days, weeks, months, or years. Determination of changes in methylation can be useful for providing diagnoses; prognoses; therapy selection; and monitoring progression for various diseases; and, in the case of cancer, tumor typing and staging. While the methods of the invention also provide for the detection of specific methylation events, the present methods are particularly notable because they are not limited by a prediction or expectation that the methylation state of a particular nucleotide is determinative of a phenotype. In cases where the density of methylation (rather than the presence or absence of a particular methylated nucleotide) modulates gene expression, and where the methylation density of a locus reflects disease progression along a continuum, the present methods are particularly helpful.

Amplification primers can be designed to amplify loci associated with a particular phenotype or disease.

If desired, multiplex DNA methods can be used to amplify multiple targets from the same sample. The additional targets can represent controls (e.g., from a locus of known methylation status) or additional loci associated with a phenotype or disease.

In some embodiments, the methods of the invention are used to identify new loci associated with a disease phenotype, such as cancer, or are used to validate such an association.

J. Detection of Methylation Density

In some embodiments, the methods of the invention can be used to determine the methylation density of a locus. Determination of methylation density is described, e.g., in U.S. patent application Ser. No. 10/971,986, filed Oct. 21, 2004.

The quantity of methylation of a locus of DNA can be determined by providing a sample of genomic DNA comprising the locus, cleaving the DNA with a restriction enzyme that is either methylation-sensitive or methylation-dependent, amplifying the DNA such that digested fragments are underrepresented and undigested fragments are overrepresented in the final amplification population and then quantifying a specific sequence in the amplified population, thereby determining the amount of intact DNA at the DNA locus of interest (i.e., corresponding to the specific sequence used in the quantification step). The amount of intact or digested DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact or digested DNA to a control value representing the quantity of intact or digested DNA in a similarly-treated DNA sample. As discussed below, the control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved, subsequently quantifying the remaining intact copies, and comparing the quantity to a control, average methylation density of a locus may be determined. If the methylation-sensitive restriction enzyme is contacted to copies of a DNA locus (where there is more than one MSRE site per locus) under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA spanning the locus will be inversely proportional to the methylation density of the locus, and thus may be compared to a control to determine the relative methylation density of the locus in the sample.

The average methylation density within a locus in a DNA sample is determined by digesting the DNA with a methylation-sensitive or methylation-dependent restriction enzyme and quantifying the relative amount of remaining intact DNA compared to a DNA sample comprising a known amount of DNA at a known methylation density according to the methods of the invention. As described above for uniformly methylated DNA, use of partial digestions allows for the determination of the average methylation density of the locus.

Either partial or complete restriction enzyme digestions, depending on the restriction enzyme, can be used to provide information regarding the methylation density within a particular DNA locus, provided that a complete digest results in at least some copies of the locus remaining intact. The restriction enzymes for use in the invention are typically selected based on a sequence analysis of the locus (or loci) of interest. One or more enzymes in each category (e.g., methylation-dependent or methylation-sensitive) are then selected. The sequence analysis can be performed based on evaluating databases of known sequences or, in some instances, can be based on empirical determinations, e.g., to take into account variants such as mutations, that may be present in a particular subject.

1. Complete Digestion

When a DNA sample comprising a locus of interest is completely digested with a methylation sensing restriction enzyme (i.e., a methylation-dependent or methylation-sensitive restriction enzyme), the information provided includes the presence or absence of methylation at recognition sequences of the restriction enzyme. The presence of intact DNA in a locus comprising the cut site of the restriction enzyme indicates that the appropriate methylation state of the recognition site necessary for cleavage by the methylation-sensitive or methylation-dependent restriction enzyme was not present at or near the locus.

The amount of intact DNA can be compared to a control representing an equal amount of DNA from the sample that was not contacted with the restriction enzyme. Alternatively, the amount of intact DNA at a locus can be compared to a second locus or to the same locus in DNA isolated from another cell. In another alternative, the amount of intact DNA at a locus can be compared to DNA having a known or expected number of methylated and monitorable restriction sites. In some embodiments, the DNA being compared is approximately the same size. Those of skill in the art will appreciate that other controls are also possible. Thus, by detecting the amount of intact DNA at the locus following restriction enzyme digestion, the relative number of methylated alleles is determined.

Use of restriction enzymes that have a variable cleavage pattern near the recognition sequence (e.g., McrBC) provides a special case for complete digestions of DNA. In this case, even if the locus contains a recognition sequence in the appropriate methylation state, some of the fragments containing a methylated locus will remain intact because cleavage of the DNA will occur outside the locus according to a function of probability. Therefore, a complete digestion with McrBC can behave similarly to a partial digestion with a methylation-sensitive restriction enzyme (which cuts at its recognition site) with respect to the number of intact alleles.

The mechanism of digesting DNA with McrBC occurs as follows. An eight subunit complex of McrB binds to each of two recognition half sites (purine-methylC represented as (A or G)mC). These complexes then recruit one McrC subunit to their respective half sites and start to translocate along the DNA mediated by GTP hydrolysis. When two McrBC bound complexes contact each other, a double-complex is formed and restriction occurs. Digestion will generally not occur if the two half sites are closer than 20 bp and restriction resulting from half sites as far as 4 kb from one another have been observed, though are rare. Restriction then occurs as a consequence of collision of the two protein complexes. It is believed that the cleavage event on each molecule occurs between the two complexes, but it may also occur outside of the two complexes and the proximity of the cut site to one particular complex is believed to be random. Therefore, it is possible for two half sites to exist within a locus and for cleavage to occur outside of the locus if one of the complexes is bound to a methylated site outside of the locus. It may be possible for the two half sites to exist outside of the locus and for a cut to occur within the locus. It is also possible for one site to exist in the locus and for another to exist outside of the locus and for a cut to occur either within or outside of the locus. Thus, the more methylated half sites that are "in the vicinity" of the locus (whether literally in the locus or in sequence flanking the locus), the more likely a cut will be observed within the locus for a given concentration of McrBC. Accordingly, the number of copies of a methylated locus that are cleaved by Ma-BC in a complete or partial digestion will be proportional to the density of methylated nucleotides recognized by McrBC.

2. Partial Digestions

The amount of cleavage with a methylation-sensitive or methylation-dependent restriction enzyme in a partial (i.e., incomplete) digestion, reflects not only the number of fragments that contain any DNA methylation at a locus, but also the average methylation density within the locus of DNA in the sample. For instance, when DNA fragments containing the locus have a higher methylation density, then a partial digestion using a methylation-dependent restriction enzyme will cleave these fragments more frequently within the locus. Similarly, when DNA fragments containing the locus have a lower methylation density, then a partial digestion using a methylation-dependent restriction enzyme will cleave these fragments less frequently within the locus, because fewer recognition sites are present. Alternatively, when a methylation-sensitive restriction enzyme is used, DNA fragments with a higher methylated density are cleaved less, and thus more intact DNA strands containing the locus are present. In each of these cases, the digestion of DNA sample in question is compared to a control value such as those discussed above for complete digestions.

In some embodiments, the DNA sample can be split into equal portions, wherein each portion is submitted to a different amount of partial digestion with McrBC or another methylation-dependent restriction enzyme. The amount of intact locus in the various portions can be compared to a control population (either from the same sample representing uncut DNA or equivalent portions from another DNA sample). In cases where the equivalent portions are from a second DNA sample, the second sample can have an expected or known number of methylated nucleotides (or at least methylated restriction enzyme recognition sequences) or, alternatively, the number of methylated recognition sequences can be unknown. In the latter case, the control sample will often be from a sample of biological relevance, e.g., from a diseased or normal tissue, etc.

In some embodiments, the DNA sample is partially digested with one or more methylation-sensitive restriction enzymes and then amplified to identify intact loci. Controls in these cases are similar to those used for methylation-dependent restriction enzyme digestions described above. Untreated controls are undigested, and any treated control DNA samples are digested with methylation-sensitive restriction enzymes.

It can be useful to test a variety of conditions (e.g., time of restriction, enzyme concentration, different buffers or other conditions that affect restriction) to identify the optimum set of conditions to resolve subtle or gross differences in methylation density among two or more samples. The conditions may be determined for each sample analyzed or may be determined initially and then the same conditions may be applied to a number of different samples.

3. Generation of Control Values

Control values can represent either external values (e.g., the number of intact loci in a second DNA sample with a known or expected number of methylated nucleotides or methylated restriction enzyme recognition sequences) or internal values (e.g., a second locus in the same DNA sample or the same locus in a second DNA sample). While helpful, it is not necessary to know how many nucleotides (i.e., the absolute value) in the control are methylated. For example, for loci in which methylation results in a disease state, knowledge that the locus is more methylated than it is in normal cells can indicate that the subject from which the sample was obtained may have the disease or be in the early stages of developing disease.

In cases where the same DNA sample includes an internal control locus, the two loci (e.g., the target and control loci) can be quantified during the quantification step by using two quantifying polynucleotides, one which hybridizes to the target sequence, and one which hybridizes to the control sequence. In this way, a target sequence and a second sequence (i.e., a control sequence) from the same sample can be quantified at the same time from the same sample.

DNA samples can vary by two parameters with respect to methylation: (i) the percentage of total copies in a population that have any methylation at a specific locus, and (ii) for copies with any DNA methylation, the average methylation density among the copies. It is ideal, though not required, to use control DNAs that evaluate both of these parameters in a test sample.

Control DNAs with known methylated cytosines are produced using any number of DNA methylases, each of which can have a different target methylation recognition sequence. This procedure can create a population of DNA fragments that vary with respect to the methylation density (i.e., the number of methylated cytosines per allele). Partial methylase reactions can also be used, e.g., to produce a normally distributed population with a mode at the average methylation density for the population. In some embodiments, the mode can be adjusted for a given population as a function of the completeness of the methylase reaction. Control DNAs can also be synthesized with methylated and unmethylated DNA bases.

In some cases, a DNA target with a known sequence is used. A desired control DNA can be produced by selecting the best combination of methylases and restriction enzymes for the analysis. First, a map of sites that can be methylated by each available methylase is generated. Second, a restriction map of the locus is also produced. Third, methylases are selected and are used to in vitro methylate the control DNA sample to bring about a desired methylation pattern, which is designed to perform optimally in combination with the restriction enzymes used in the methylation analysis of the test DNA and control DNA samples. For example, M.HhaI methylates the site (G*CGC) and McrBC recognizes two half sites with the motif (RpC). Therefore, each methylated M.HhaI site in the control sequence is recognized by McrBC.

Similarly, a population of molecules may be then treated with a DNA methylase (e.g., M.Sss1) in the presence of magnesium to result in a desired methylation density. If the reaction is allowed to run to completion, nearly all of the sites that can be methylated will be methylated, resulting in a high and homogeneous methylation density. If the reaction is limited in its course, a lower average methylation density (or partial methylation) will result (i.e., all possible sites are not methylated due to timing of reaction and/or concentration of enzyme). In this way, the desired average methylation density of the control DNA can be produced. The methylated control DNA can be precisely characterized by determining the number of methylated cytosines through bisulfite sequencing. Alternatively, the methylation control DNA can be precisely characterized by determining the number of methylated cytosines through a comparison to other known control DNAs as described herein.

For more precise prediction of methylation densities, it may be useful to generate a control set of DNA that can conveniently serve as a standard curve where each sample in the control set has a different methylation density, either known or unknown. By digesting the multiple samples with a methylation-dependent restriction enzyme or a methylation-sensitive restriction enzyme under conditions that allow for at least some copies of potential restriction enzyme cleavage sites in the locus to remain uncleaved and subsequently amplifying the remaining intact copies of a locus, a standard curve of the amount of intact copies can be generated, thereby correlating the amount of intact DNA to different methylation densities. The standard curve can then be used to determine the methylation density of a test DNA sample by interpolating the amount of intact DNA in the sample following restriction and amplification as described herein.

4. Calculation of Methylation Density Based on Cycle Thresholds

Quantifying the amount of a specific sequence in the final amplified population thereby quantifying the number of intact copies of a locus after the digesting step, and comparing these quantities enable one to calculate the methylation density of a locus in a sample. Accordingly, the number of intact copies from samples treated with a methylation-dependent and/or methylation-sensitive restriction enzyme can be used to calculate methylation density. A change in the number of intact copies between one sample and a control value (which can represent the number of intact copies from a second sample) is predictive of relative methylation density.

K. Uses for Amplified Methylated or Unmethylated DNA

The amplified DNA produced according to the methods of the invention can be used to generate additional tools for analysis of genomic DNA (e.g., libraries), to identify the methylation profiles of multiple cell populations, to identify unmethylated or methylated genes, and to identify genetic polymorphisms, including single nucleotide polymorphisms (SNPs).

The present invention can also be used to screen organisms or cells for desired or unknown genotypes. Exemplary cells include stem cells, including adult or fetal stem cells, or any other cell or organism where somaclonal variation can occur within a population. Thus, the present invention allows one to monitor for the presence of variation and to select individuals that have or lack that variation. Similarly, methylation profiles of diseased cells (e.g., cells from a plant that is developmentally delayed, cancer cells, cells from an individual with vascular disease, cells from an individual with a cognitive disorder or cells suspected of being diseased) can be determined for use, e.g., in diagnosis and treatment of a disease or disorder.

In mammalian cells, DNA methylation involves the enzymatic transfer of a methyl group to the C5 position of cytosines within CpG dinucleotides. These dinucleotides are generally underrepresented across the genome, with the exceptions of low sequence complexity elements and "CpG islands" associated with the promoter regions of many genes (1). Methylation of these sequence elements is directly associated with regulation of gene expression via effects on local chromatin structure (2). The importance of this regulation is demonstrated by the fact that the establishment, maintenance, and interpretation of DNA methylation information are all essential for normal mammalian development (3-5).

In addition to abnormalities in the genetic code, literally every type of cancer displays global rearrangements in the epigenetic pattern of DNA methylation (i.e. the "second code"). Tumor cells exhibit global DNA hypomethylation as well as simultaneous locus-specific hypermethylation events associated with transcriptional silencing of tumor suppressor genes (6). These epigenetic abnormalities involve stable modifications of tumor cell DNA (either inappropriate gain or loss of CpG methylation) and may therefore represent powerful DNA methylation-based biomarkers that can be exploited for non-invasive disease detection, prognosis and therapeutic design. A critical step in the realization of this goal is the elucidation of disease-specific abnormalities in DNA methylation patterns.

In addition to cancer recent hypotheses concerning all the aquired common diseases (heart disease, diabetes, etc) posit that the epigenetic contribution to these diseases is substantial (Bjornsson et al., (2004) Trends Genet. 20(8):350-8. Interpretation of the extreme of this notion posits that DNA methylation alterations underlie the molecular defects in these complex diseases.

The present invention can identify multiple aberrant events occurring in tumorigenesis and tumor progression, or in any other epigenetic disease. The invention provides the capacity to discover epigenetic changes (i.e., DNA methylation changes). The invention also provides a capacity to detect changes at multiple loci in parallel. This invention has the capacity simultaneously measure patterns of methylation changes, or changes in DNA methylation at $10^0$, $10^1$, $10^2$, $10^3$, $10^4$, $10^5$, $10^6$, $10^7$, $10^8$ or more loci. This invention is useful for DNA methylation based biomarker discovery as well as to serve as the platform for molecular diagnostic tests.

One amplification reaction is required for each digestion condition per DNA sample, regardless of whether methylation at 1 or 1 million loci was being tracked. This invention allows one to minimize the sample DNA required. For instance, in the case of early cancer detection tumor DNA has been discovered to be circulating in the blood and this DNA can be recovered from serum. Clinical samples, for example, may have as little as 1 nanogram of DNA. The present invention has the potential to monitor DNA methylation simultaneously at every human in a 1 ng sample.

L. Libraries of Methylated or Unmethylated DNA

The amplified DNA produced according to the methods of the invention can be cloned as individual sequences or into libraries.

The clones can also be sequenced using methods known in the art to obtain the complete or partial sequences of genomic DNA (e.g., from a plant cell, from an animal cell, from a fungus cell, or from a prokaryotic cell). Suitable sequencing methods are described in, e.g., Ausebel et al., supra and Sambrook et al., supra.

In another embodiment, the methods of the invention can be used to determine a complete sequence of the transcriptional units of a genome.

In one such aspect, the amplified intact DNA is further modified to form concatenated DNA sequences. The amplified intact DNA is contacted with a restriction enzyme that recognizes a site within the adaptor and cuts within the intact amplified DNA. Suitable restriction enzymes include those which cut rarely, such as intron encoded endonucleases which have large, asymmetric recognition sites of about 12 to about 40 base pairs (e.g., I-Ceu I, I-Sce I, I-Sce-II, I-Tev-I, I-Tev-II, I-Cre-I, PI-Psp I, PI-Sce I, and I-Ppo1) (see, Belfort and Roberts, *Nucleic Acids Res.* 25:3379-3388 (1997) and Lowery et al., *Promega Notes Magazine* 38:8 (1992)), to generate fragments of amplified intact unmethylated or methylated DNA (e.g., typically of about 100 to about 1000 or about 200 to 1000 nucleotides in length.

In another alternative, fragments are generated in a modification of the method described in, e.g., Velculescu et al., *Science,* 270(5235):484-487 (1995). That is, amplified intact DNA comprises a sequence tag that contains a recognition sequence of a Type IIS restriction enzyme. The Type IIS enzyme recognizes the sequence tag but cuts DNA at some short distance away from the sequence tag, thereby producing a fragment comprising the sequence tag and some sequence of the amplified intact DNA.

In either of the above embodiments, the fragments of amplified intact DNA are subsequently ligated to each other to generate concatenated DNA sequences. One of skill in the art will appreciate that the fragments of amplified intact DNA can be "polished" to create blunt ends prior to ligation. In some embodiments, the concatenated DNA sequences are ligated to each other via polynucleotide linkers of about 5 to about 15 bases in length. The concatenated DNA sequences can be cloned into a library for further analysis. The concatenated DNA sequences can conveniently be sequenced to identify the unmethylated or methylated sequence of a genome. For example, in a single sequencing run, it may be possible to obtain sequence information from 2, 3, 4, 5, 6, 7, 8, 9 10, or more different fragments within one concatenated DNA sequence. By sequencing numerous clones, it is possible to determine the presence, absence and abundance of any particular unmethylated or methylated sequence in a sample. By comparing concatenated DNA sequences derived from the genome of more than one individual, genetic polymorphisms can be identified.

M. Kits

The present invention also provides kits for performing the methods of the invention. For example, the kits of the invention can comprise, e.g., a methylation-dependent restriction enzyme and/or a methylation-sensitive restriction enzyme, a methylation-insensitive restriction enzyme, amplification reagents (i.e., DNA polymerase, nucleotides, buffers, primers (either random or specific)), ligase, sequence adaptors, N-terminal transferase, shearing reagents (chemicals or enzymes used in shearing), labeling reagents (i.e., modified nucleotides that can provide a basis for subsequent detection (biotin or fluorogenic moieties), control DNA samples (i.e., samples comprising a pre-determined number of methylated nucleotides at a locus, and/or comprising a predetermined number of total copies of a locus, and/or comprising a predetermined number of methylated copies of a locus and/or comprising a predetermined number of unmethylated copies of a locus), and/or reagents for the quantification of specific sequences in the amplified population (i.e., polynucleotides bound to solid substrates, or used in additional amplification steps etc.), and/or one or several control polynucleotides that hybridize to the control loci in the test DNA sample, or to control DNA molecules.

The kits of the invention will often contain written instructions for using the kits. The kits can also comprise reagents sufficient to support the activity of the restriction enzyme. The kits can also include a thermostable DNA polymerase or other polymerases used in amplification.

In some cases, the kits also comprise one or two different target polynucleotide primers that hybridize to a pre-determined region of human genomic DNA. For example, as described above, the primers can allow for amplification of loci associated with the development or prognosis of disease.

In some embodiments, the kits may comprise one or more detectably-labeled polynucleotide probes to monitor amplification of target polynucleotides.

In some embodiments, the kits comprise at least one target polynucleotide that distinguishes between modified unmethylated and methylated DNA in human genomic DNA.

In some embodiments, the kits also typically include a fluorescent moiety that allows the kinetic profile of any amplification reaction to be acquired in real time.

In some embodiments, the kits may comprise at least one target polynucleotide primer that distinguishes between modified unmethylated and methylated DNA in human genomic DNA. In these embodiments, the kits will also typically include an agent that modifies unmethylated cytosine, and the reagents necessary to support the recovery of such modified DNA.

In some embodiments, the kits may also comprise an RNA probe, and the reagents necessary to produce cRNA from DNA (e.g., promoter containing sequence tags, RNA polymerase, ATP, UTP, CTP and GTP, RNA polymerase buffer, RNAse inhibitors), a binding and or quantifying polynucleotide that specifically binds RNA:DNA complexes, detection reagents recognizing RNA:DNA hybrids (e.g., an antibody or an antibody mimetic), and methylation-sensitive, methylation-dependent restriction enzymes and methylation-insensitive restriction enzymes.

EXAMPLES

Example 1

Generating and Analyzing Six Portions from a First Sample

DNA is obtained from a glioma derived human tumor cell line (ATCC catalogue #2610). 10 ug of the DNA is sheared in a 300 ul volume of water using GeneMachine's hydroshear for 20 cycles at speed code setting 5. An aliquot of sheared DNA is loaded onto an agarose gel and the mode of the ethidium staining is determined to be between 500 and 2,000 bp. The DNA is concentrated on a speed vac to an appropriate concentration just below 1 ug/ul as determined by a spectrophotometer using absorbance readings at 260 and 280 nm.

40 ul are placed into two microcentrifuge tubes. One tube is carried forward and the remainder is frozen at −20 deg C. and would serve as the unamplified control later. 40 ul of the DNA undergoes end-repair using the End-it kit from Epicentre (Madison Wis.) according to the manufacturer's instructions, and was cleaned using MinElute Reaction Cleanup Kit (Qiagen #28206).

Two oligos, A and B, are synthesized with the following primary sequences:

```
                                       (SEQ ID NO: 1)
Oligo A 5'CATGGCCTATAGTGAGTCGTATTACAATTC-3',
and (SEQ ID NO: 2)
Oligo B 5'TTTGAATTGTAATACGACTCACTATAGGCCATG-3'.
```

10 ul of Oligo A (0.1 mM in TE and 30 ul of water is added to 10 ul of Oligo B (0.1 mM in TE). The primers are incubated 2 min at 95° C., 10 min at 65° C., 10 min at 37° C., 20 min at 25° C. and 10 min at 4° C., allowing the primers to anneal/base-pair to each other specifically and creating double stranded sequence tag adapters. 100 pmoles of the adapters is ligated onto the sheered and end repaired genomic DNA using the Epicenter Fast-link ligation protocol under the manufacturer's specified conditions. A large stoichiometric excess of adapters molecules to template molecules is used to avoid catenation of genomic DNA fragments. The ligations are cleaned using MinElute Reaction Cleanup Kit (Qiagen #28206).

The ligated products are verified by employing a PCR reaction using primers specific to the adapters. PCR amplifications of genomic DNA that had been ligated are compared to genomic DNA that had not been ligated as a control. Significant amplification is observed in the ligated reaction while no amplification is observed in the no-ligation control.

The ligated DNA is then split into five portions. 200 ng of the ligated DNA is added to each of tubes #1-#5. Tube #6 receives 200 ng of un-ligated sheared genomic DNA. Four enzyme digests are conducted (in tubes 1-4) and two "mock" (all components except restriction enzymes are added) digests are conducted (tubes #5 and 6). All digests use NEB buffer 2 and are supplemented with BSA as suggested by NEB. In addition the reactions contain 1 mM GTP.

To tube 1, we add 20 U of HpaII, to Tube #2, 20 U of MspI, to Tube #3, 20 U of McrBC, to Tube #4, 10 U of HpaII and 10 U of McrBC, and to Tubes #5 and 6, no restriction enzymes are added. The reactions ware allowed to incubate for three hours at 37 deg C. and are terminated with heat treatment at 60 deg C. for 30 minutes.

Approximately 20 ng of DNA iss removed from each of the six tubes. PCR reactions are carried out in on DNA from tubes 1-5 at 50 ul volumes using 200 pmoles of a PCR primer complementary to the sequence tag adapter (e.g., Oligo A+Oligo B), a 2×PCR Epicenter Failsafe premix C, and the manufacture's recommended amount and concentration of TAQ polymerase. The cycling parameters are:

incubation for 2 min at 94 degrees C.,
followed by 25 cycles at: 94 degrees C. for 15 sec, 55 degrees C. for 15 sec, 72 degrees C. for 1 min,
followed by incubation at 72 degrees C. for 3 min.

The PCR reaction is desalted and concentrated with a Qiaquick PCR purification kit (Qiagen #28106), and the concentration of amplified DNA is determined by absorbance spectrophotometry.

500 ng from each amplification reaction (tubes 1-5), and 500 ng from the unamplified undigested DNA in tube 6 undergoes random primer mediated direct incorporation labeling using the Invitrogen Bio-primer kit supplemented with 1 mM Cy3-dCTP using the manufacturer's recommended conditions. The 6 labeled targets are then hybridized to 6 Agilent's in situ synthesized 60 mer Human v2 arrays (cat #G4110B) and the arrays are washed and scanned using Agilent's recommended protocols, and six array files were generated. Relative quantifications of specific sequence are determined for each of the six array files.

Example 2

Utilizing Exonucleases to Remove Digested DNA Products and Lower Background Signal in the Quantifying Step In this example, a cocktail of exonucleases is used to degrade digested DNA fragments, leaving the undigested DNA fragments intact and available for participation in the amplification reaction.

The procedure set forth in Example 1 is performed on DNA from the same sample. However, prior to the digestion step, the sample is dephosphorylated using shrimp alkaline phosphatase under the conditions specified by USB, in order to protect the ends of the molecules from attack by lambda exonuclease. The phosphatase is then heat inactivated. Note that synthetic polynucleotides that are used as adaptors can offer protection against lambda nuclease attack. Note also that Exonuclease III can be used but in this case an overhang of 4 or more nucleotides from 3' end of DNA created by certain restriction enzyme, by terminal transferase or by synthetic adaptors will work as protection against ExoIII attack. One of skill in the art would recognize that it is possible to use terminal transferase and any dNTP to create a 3' overhang, and then remove the adapters. This will similarly and more effectively protect the adapted ends of the fragments from lambda exonuclease.

Following restriction digestion, lambda exonuclease along with relevant buffers and salts are added to each of the digests according to the manufacturer's suggestions. The lambda exonuclease will completely degrade DNA strands with a free 5' phosphate leaving the second strand of DNA as a single strand. Then lambda exonuclease is heat inactivated for 10 min at 75° C. and exonuclease 1 is added to each of the digests along with additional salts to make up the proper buffer according to the manufacturer's suggestions. Exonuclease I will then degrade the remaining single-strand. Note that other exonuclease specific to single strand DNAs could be used (e.g., Mung Bean nuclease) In this way fragments that are digested by any of the restriction enzymes used in the digests (i.e., the HpaII, Mspl, or McrBC) can then be completely destroyed. The samples are amplified, labeled and hybridized to Agilent arrays, and specific sequences are quantified in each hybridized array as in the above example.

Optionally, the exonuclease treatment step can also be performed after the amplification step. Exonuclease 1 along with relevant buffers and salts are added to each of the digests according to the manufacturer's suggestions. Treatment following amplification will destroy the accumulated linear amplification products and can improve signal to noise ratios on the array.

Example 3

Comparison of Portions from a First Sample to Portions from a Second Sample

The procedure set forth in Example 1 is repeated on a second sample (Male blood genomic DNA purchased from Novagen, Madison Wis.). Specific sequences are quantified from the six array files of the second sample and are compared to the same specific sequences quantified from six array files generated from the first sample.

Example 4

Adding and Using Poly a Sequence Tags to Amplify Portions

Sample DNA is obtained, sheared, recovered and quantified according to the methods set forth in Example 1.

15 ul is placed into two microcentrifuge tubes. One tube is carried forward and the remainder is frozen at −20 deg C. and serve as the unamplified control later. 5 ul of the DNA undergoes end-repair using the End-it kit from Epicentre (Madison Wis.) according to the manufacturer's instructions.

DNA is treated with terminal transferase (TdT Roche #3333566) along with suggested buffer and dATP (the dATP is used at a 0.6 uM final concentration). The reaction is incubated at 37° C. for 15 min, and is cleaned up using MinEluteReaction Cleanup kit (Qiagen #28206).

The tailed DNA is annealed to and then ligated with 1 pmol of an oligonucleotide using Taq ligase (NEB #MO208S) according to the manufacturer's instructions. The ligation reaction is incubated in a step wise fashion under the following conditions:

60° C. for 5 min, 45° C. for 15 min, 37° C. for 10 min, 34° C. for 10 min 25° C. for 10 min and 60° C. for 10 min.

The ligated oligonucleotide has the following sequence:

(SEQ ID NO: 3)
5' AGTGGTAACAACGCAGAGTACTTTTTTTTTTTTTTTVN-3', where A, C, G, and T represent specific DNA bases, V represents a random addition of G, A, or C, and N represents a random addition of G, A, T or C.

The tailed DNA is then split into five portions. 200 ng of the ligated DNA is added to each of tubes #1-#5. Tube #6 received 200 ng of un-ligated sheared genomic DNA. Four enzyme digests are conducted (in tubes 1-4) and two "mock" (all components except restriction enzymes are added) digests are conducted (tubes #5 and 6). All digests use NEB buffer 2 and are supplemented with BSA as suggested by NEB. In addition the reactions contains 1 mM GTP.

To tube 1, we add 20 U of HpaII, to Tube #2, 20 U of Mspl, to Tube #3, 20 U of McrBC, to Tube #4, 10 U of HpaII and 10 U of McrBC, and to Tubes #5 and 6, no restriction enzymes are added. The reactions are allowed to incubate for three hours at 37 deg C. and are terminated with heat treatment at 60 deg C. for 30 minutes.

Approximately 20 ng of DNA is removed from each of the six tubes. PCR reactions are carried out in on DNA from tubes 1-5 at 50 ul volumes using 200 pmoles of a PCR primer complementary to the poly a tail sequence tag, a 2×PCR Epicenter Failsafe premix C, and the manufacture's recommended amount and concentration of TAQ polymerase. The cycling parameters are:

incubation for 2 min at 94° C.,
followed by 3 cycles at: 94° C. for 15 sec, 34° C. for 15 sec, 72° C. for 1 min,
followed by 20 cycles at: 94° C. for 15 sec, 60° C. for 15 sec, 72° C. for 1 min,
followed by incubation at 72° C. for 5 min.

The PCR reaction is desalted and concentrated with the Qiaquick PCR purification kit (Qiagen #28106), and the concentration of amplified DNA is determined by absorbance spectrophotometry.

500 ng from each amplification reaction (tubes 1-5), and 500 ng from the unamplified undigested DNA in tube 6 undergoes random primer mediated direct incorporation labeling using the Invitrogen Bio-primer kit supplemented with 1 mM Cy3-dCTP using the manufacturer's recommended conditions. The 6 labeled targets are then hybridized to 6 Agilent's in situ synthesized 60 mer Human v2 arrays (cat #G4110B) and the arrays are washed and scanned using the Agilent's recommended protocols, and six array files are generated. Relative quantifications of specific sequence are determined for each of the six array files.

Example 5

Analyzing Non-Randomly Fragmented DNA

DNA is obtained from a glioma derived human tumor cell line (ATCC catalogue #2610). The restriction enzyme MboI and the appropriate buffers are added to the sample DNA, and the sample is digested. Aliquots are removed from the digestion reaction, each to a separate tube over a time course and the removed aliquots are immediately heat denatured. Aliquots of DNA from each digestion time point are analyzed by agarose gel electrophoresis, and a time point is selected which there is substantial digestion yet very little accumulation of completely digested products.

40 ul is placed into two microcentrifuge tubes. One tube is carried forward and the remainder is frozen at −20 deg C. and would serve as the unamplified control later. 40 ul of the DNA undergoes end-repair using the End-it kit from Epicentre (Madison Wis.) according to the manufacturer's instructions, and is cleaned using MinElute Reaction Cleanup Kit (Oiagen #28206).

Two oligos, B (See Example 1) and C, are synthesized with the following primary sequences:

(SEQ ID NO: 4)
Oligo C 5'GCCTATAGTGAGTCGTATTACAATTCGATC-3'

The tag adaptors are manufactured as described in Example 1 and ligated onto the end of 40 ul of cut DNA using the Epicenter Fast-link ligation protocol under the manufacturer's specified conditions. The ligated products are verified as described in Example 1.

The ligated DNA is then split into five portions and treated with restriction enzymes (MspI, HpaII, and McrBC) as described in Example 1.

Approximately 20 ng of DNA is removed from each of the six tubes. PCR reactions are carried out in on DNA from tubes 1-5 at 50 ul volumes using 200 pmoles of a PCR primer complimentary to the sequence tag adapter (e.g., Oligo C+Oligo B), a 2×PCR Epicenter Failsafe premix C, and the manufacture's recommended amount and concentration of TAQ polymerase. The cycling parameters are:

incubation for 2 min at 94° C.,
followed by 25 cycles at: 94° C. for 15 sec, 60° C. for 15 sec, 72° C. for 1 min,
followed by incubation at 72° C. for 5 min.

The PCR reaction iss desalted and concentrated with the Qiaquick PCR purification kit (Qiagen #28106), and the concentration of amplified DNA is determined by absorbance spectrophotometry.

500 ng from each amplification reaction (tubes 1-5), and 500 ng from the unamplified undigested DNA in tube 6 undergoes random primer mediated direct incorporation labeling as described in Example 1.

In the above example, the sequence tag adapters can also be added to the 5 portions after the 4 enzyme treatments and 1 mock treatment. This is done by adding sequence tag adapters that are compatible with the fragmenting restriction enzyme (i.e., have the same 'sticky end') and are not compatible with the methylation-sensitive, methylation-dependent, or methylation-insensitive restriction enzymes (i.e., have 'different ends'). To accomplish this, the restriction enzyme used in the fragmenting step is selected such that it generates DNA ends that are incompatible with the DNA ends generated by the restriction enzymes used in the subsequent digestion conducted on tubes 1-4. After the second digestion step, the ends generated by the fragmenting restriction enzyme, and the restriction enzymes used in tubes 1-4 must also be dephosphorylated with shrimp alkaline phosphatase at 37 degrees C. for 30 minutes and heat denatured for 30 minutes at 65 degrees C. The sequence tag adaptors (e.g., the annealed Oligos C and D) are blocked at the 5 prime end (i.e., with a thiol group).

Finally, the ligation reaction and all following steps occur in the same manner as written above.

Example 6

Utilizing Random Priming Mediated Amplification

DNA is obtained from a glioma derived human tumor cell line (ATCC catalogue #2610). 10 ug of the DNA is sheered in a 300 ul volume of water using GeneMachine's hydrosheer for 20 cycles at speed code setting 5. An aliquot of sheared DNA is loaded onto an agarose gel and the mode of the ethidium staining is determined to be between 500 and 2,000 bp. The DNA is concentrated on a speed vac to an appropriate concentration just below 1 ug/ul as determined by a spectrophotometer using absorbance readings at 260 and 280 nm.

40 ul or the sheared DNA is placed into two microcentrifuge tubes. One tube is carried forward and the remainder is frozen at −20 deg C. and serves as the unamplified control later.

Random oligos are synthesized according to standard procedures. For optimum selective amplification of higher molecular weight digested DNA fragments over lower molecular weight digested DNA fragments, different oligo lengths are used ranging from random pentamers to random dodecamers.

The sheared DNA is then split into five portions. 200 ng of the DNA is added to each of tubes #1-#5. Tube #6 receives 200 ng of unsheared DNA. Four enzyme digests are conducted (in tubes 1-4) and two "mock" (all components except restriction enzymes are added) digests we conduct (tubes #5 and 6). All digests use NEB buffer 2 and are supplemented with BSA as suggested by NEB. In addition the reactions contain 1 mM GTP.

To tube 1, we add 20 U of HpaII, to Tube #2, 20 U of MspI, to Tube #3, 20 U of McrBC, to Tube #4, 10 U of HpaII and 10 U of McrBC, and to Tubes #5 and 6, no restriction enzymes are added. The reactions are allowed to incubate for three hours at 37 deg C. and are terminated with heat treatment at 60 deg C. for 30 minutes.

Approximately 20 ng of DNA is removed from each of the six tubes and PCR reactions are carried out in on DNA from tubes 1-5 using quantities of the random primer and PCR conditions standard for random primer based amplification. The PCR reaction is desalted and concentrated with the Qiaquick PCR purification kit (Qiagen #28106), and the concentration of amplified DNA is determined by absorbance spectrophotometry.

500 ng from each amplification reaction (tubes 1-5), and 500 ng from the unamplified undigested DNA in tube 6 undergoes random primer mediated direct incorporation labeling using the Invitrogen Bio-primer kit supplemented with 1 mM Cy3-dCTP using the manufacturer's recommended conditions. The 6 labeled targets are then hybridized to 6 Agilent's in situ synthesized 60 mer Human v2 arrays (cat #G4110B) and the arrays are washed and scanned using the Agilent's recommended protocols, and six array files are generated. Relative quantifications of specific sequence are determined for each of the six array files.

The above example can also utilize hybrid random-defined primers (i.e., oligonucleotide primers that have a random sequence motif on the 3' end and a defined sequence motif on the 5' end). After a few rounds of random amplification with the hybrid random-defined primer, the defined sequence can serve as a sequence tag to drive amplification in a targeted manner. To accomplish this, a second round of PCR primers complementary to the defined sequence motif are added whole genome amplification was conducted.

The labeling reaction and subsequent hybridization to a microarray can be conducted as outlined above.

Example 7

Comparison to Identify Methylation at a Locus

The following example illustrates how the methods of the invention can be used to determine the relative number of methylated copies of a locus, the relative number of unmethylated copies of a locus, the relative number of hemimethylated copies of a locus, the relative number of mutated copies of a locus, and the relative total number of copies of a locus in a DNA sample. DNA is isolated from a sample and divided into portions, each of which contains all of the sequences present in the sample. This example uses the restriction site for Sau3A I for illustrative purposes and monitors 6mA methylation. One of skill in the art will appreciate that different enzymes could be selected to monitor cytosine methylation. Some methylation-sensitive restriction enzymes are blocked by both hemi-methylated and fully-methylated recognition sites, while other methylation-sensitive restriction enzymes are blocked only by fully-methylated recognition sites. One of skill in the art will appreciate that each combination of restriction enzymes used will establish a unique paradigm of which classes of locus methylation will survive a given restriction digest thereby altering the mathematics required to solve for any given methylation state. This example illustrates one such selection of restriction enzymes and one such set of equations.

Any given restriction site has three potential states: (1) hemimethylated; (2) methylated; (3) unmethylated; and (4) mutated.

```
1.     G*ATC = hemimethylated ("hemi")
       C TAG

2.     G*AT C = fully-methylated ("meth")
       C TA*G

3.     GATC  = unmethylated ("unmeth")
       CTAG

4.     G TTC = mutated ("mut")
       C AAG
```

Sau3A I is a methylation insensitive restriction enzyme which cuts when a fully-methylated (e.g., methylation is on both strands) or hemi-methylated (e.g., methylation is on only one strand) adenosine residue is at its recognition site. Dpn I is a methylation-dependent restriction enzyme which cuts only when a fully-methylated adenosine residue is at or near its recognition site. Mbo I is a methylation-sensitive enzyme that does not cut when a methylated adenosine residue is at its recognition site, and is also the isoschizomer of Sau3A I. Hemimethylated sites are cut by Sau3A U, but not by Dpn I or Mbo I; fully-methylated sites are cut by Dpn I and Sau3A I, but not by Mbo U; and unmethylated sites are cut by Sau3A I and Mbo I, but not by Dpn I.

A. Hybridization of a quantifying polynucleotide to the amplified intact DNA fragments in the first portion of an untreated DNA sample, or mock treated DNA sample, or hybridization of a quantifying polynucleotide to the unamplified DNA fragments in the sixth portion of an untreated DNA sample, or mock treated DNA sample, yields the total number of copies of the locus in the sample, which equals:
(1) hemi+(2) meth+(3) unmeth+(4) mut.

B: Hybridization of a quantifying polynucleotide with the same sequence as the locus to the amplified intact DNA fragments in the second portion of the DNA sample, where the second portion was digested with the methylation-sensitive restriction enzyme Mbo I before the amplification step, yields the number of methylated, hemimethylated and mutated copies of the locus in the sample, which equals:
(1) hemi+(2) meth+(4) mut.

C: Hybridization of a quantifying polynucleotide with the same sequence as the locus to the amplified intact DNA fragments in the third portion of the DNA sample, where the third portion was digested with the methylation-dependent restriction enzyme Dpn I before the amplification step, yields the total number of hemi methylated, unmethylated and mutated copies of the locus in the sample, which equals:
(1) hemi+(3) unmeth+(4) mut.

D. Hybridization of a quantifying polynucleotide with the same sequence as the locus to the amplified intact DNA fragments in the fourth portion of the DNA sample, where the fourth portion was digested with the methylation-sensitive restriction enzyme Mbo I, and the methylation-dependent restriction enzyme Dpn I before the amplification step, yields the total number of hemimethylated and mutated copies of the locus in the sample, which equals:
(1) hemi+(4) mut.

E: Hybridization of a quantifying polynucleotide with the same sequence as the locus to the amplified intact DNA fragments in the fifth portion of the DNA sample, where the fifth portion was digested with Sau3A 1, a methylation-insensitive restriction enzyme that is an isoschizomer of the methylation-dependent restriction enzyme (Dpn I) before the amplification step, yields the total number of mutated copies of the locus in the sample, i.e., copies which are complementary to the quantifying polynucleotide, but do not contain hemimethylated, methylated, or unmethylated restriction sites, which equals:

(4) mut.

F A comparison of the results from A and B leads to the total number of unmethylated copies of the locus in the sample:
Unmeth=A[hemi+meth+unmeth+mut]−B[hemi+meth+mut].

G. A comparison of the results from A and C leads to the total number of methylated copies of the locus in the sample:
Meth=A[hemi+meth+unmeth+mut]−C[hemi+unmeth+mut].

H A comparison of the results from A, B, and C leads to the total number of hemimethylated copies and unmethylated copies of the locus in the sample:
Hemi+unmeth=C[hemi+unmeth+mut]−(A[hemi+meth+unmeth+mut]−B[hemi+meth+mut]).
Hemi+unmeth=B[hemi+meth+mut]−(A[hemi+meth+unmeth+mut]−B[hemi+unmeth+mut]).

I. A comparison of the results from A and D leads to the total number of methylated and unmethylated copies of the locus in the sample:
Meth+unmeth=A[hemi+meth+unmeth+mut]−D[hemi+mut].

J. A comparison of the results from D and E leads to the number of hemimethylated copies of the locus in the sample:
Hemi=D[hemi+mut]−E[mut].

K. A comparison of the results from E and D with B or C leads to the number of methylated or unmethylated copies of the locus in the sample, respectively:
Meth=B[hemi+meth+mut]−E[mut]−(D[hemi+mut]−E[mut])
Unmeth=C[hemi+unmeth+mut]−E[mut]−((D[hemi+mut]−E[mut]).

Example 8

Constructing a DNA Methylation Standard Sample Set

A standard sample set is generated in numerous ways. For example, a methylase (e.g., M.SssI or other methylases such as M.HhaI, M.AluI) is applied in vitro to a series of DNA samples to produce a standard set of DNAs known to have increasing methylation densities. This standard set is generated by first obtaining a sample of known sequence (e.g., the locus of interest). Next, the sample is divided into a series of samples and each sample in the series is treated with the chosen methylase in the presence of magnesium and in a manner that results in increasing methylation densities of the samples in the series.

A partial methylation reaction refers to contacting DNA with a cocktail of one or more methylases under appropriate reaction conditions such that the methylase modifies some (e.g., about 10%, 20%, 30%, 40%, 50%, 60%, 70%, 80%, 90%) but not all of the possible methylase recognition sites for each enzyme in the methylase cocktail. A DNA sequence is partially methylated by treating DNA with an active methylase for a shorter period of time than is necessary to achieve complete methylation, and then terminating the reaction, or under other altered reaction conditions that allow for the desired amount of partial methylation.

The methylation densities of each sample in the series are measured by sequencing a statistically significant sample of clones from a bisulfite-treated portion of each series member in the set, by identifying the converted cytosines within each clone, and by calculating the average methylation density for each reaction within the methylation sample set. In order to achieve a partial methylation density on a given fragment, the methylase acts in a stochastic manner, and not a processive manner. For M.SssI, this is achieved by conducting the reaction in the presence of magnesium, since M.SssI methylates DNA in a processive way in the absence of magnesium, while in the presence of magnesium the enzyme methylates CpGs in a nonprocessive, stochastic manner.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference.

What is claimed is:

1. A method of amplifying unmethylated or methylated DNA fragments in a biological sample, the method comprising:
   (a) providing randomly fragmented DNA from the biological sample;
   (b) adding a sequence tag onto at least one end of the DNA fragments, thereby generating modified DNA fragments;
   (c) digesting the modified DNA fragments with a methylation-dependent restriction enzyme under conditions where the resulting number of intact modified DNA fragments is inversely proportional to the methylation density of the locus or a methylation-sensitive restriction enzyme under conditions where the resulting number of intact modified DNA fragments is directly proportional to the methylation density of the locus to obtain intact modified DNA fragments and digested DNA fragments; and
   (d) after the digesting step, amplifying the intact modified DNA fragments with at least one primer that initiates amplification from the sequence tags, thereby generating amplified intact DNA fragments representing the unmethylated or methylated modified intact DNA fragments in the sample.

2. The method of claim 1, comprising randomly fragmenting DNA from the biological sample before the adding step.

3. The method of claim 1, wherein the adding step comprises ligating the sequence tag to at least one end of the DNA fragments.

4. The method of claim 1, wherein the sequence tags comprise synthetic molecules that exhibit base pairing.

5. The method of claim 4, wherein the synthetic molecules are selected from the group consisting of peptide nucleic acids and intercalating nucleic acids.

6. The method of claim 1, wherein the adding step comprises adding a homopolymeric sequence tag to at least one of the ends of the DNA fragments with terminal transferase.

7. The method of claim 1, wherein the digesting step comprises digesting the fragmented DNA with a methylation-sensitive restriction enzyme; and the amplifying step comprises amplifying intact modified fragments having the same sequence as the methylated DNA in the sample.

8. The method of claim 1, wherein the digesting step comprises digesting the fragmented DNA with a methylation-dependent restriction enzyme; and the amplifying step comprises amplifying intact modified fragments having the same sequence as the unmethylated DNA in the sample.

9. The method of claim 1, wherein the amplifying step comprises the polymerase chain reaction.

10. The method of claim 1, wherein the amplifying step comprises rolling circle amplification or branched chain amplification.

11. The method of claim 1, wherein the amplification is linear.

12. The method of claim 1, wherein the method comprises quantifying the number of amplified intact DNA fragments comprising a particular sequence.

13. The method of claim 12, wherein the quantifying step comprises hybridizing the amplified intact DNA to a quantifying polynucleotide.

14. The method of claim 13, wherein the quantifying polynucleotide comprises synthetic molecules that exhibit base pairing.

15. The method of claim 14, wherein the synthetic molecules are selected from the group consisting of peptide nucleic acids and intercalating nucleic acids.

16. The method of claim 13, wherein the quantifying step is performed after the amplifying step and the quantifying step comprises detecting copies of a locus with hybrid capture.

17. The method of claim 13, wherein the quantifying polynucleotide is used in a quantitative amplification step.

18. The method of claim 13, wherein the quantifying polynucleotide is attached to a solid support.

19. The method of claim 13, wherein, before the amplifying step, the DNA fragments are contacted with an agent that modifies unmethylated cytosines but does not modify methylated cytosines; and the quantifying step comprises hybridizing a polynucleotide to amplified intact DNA where the polynucleotide hybridizes to the converted sequence.

20. The method of claim 1, further comprising sequencing the amplified intact DNA fragments.

21. The method of claim 1, wherein the method further comprises cloning the amplified DNA to make a library of sequences representing the unmethylated or methylated DNA in the sample.

22. The method of claim 1, wherein the methylation is at the C5 position of a cytosine within the locus.

23. The method of claim 8, wherein the methylation-dependent restriction enzyme is McrBC.

* * * * *